(12) United States Patent
Li et al.

(10) Patent No.: US 11,180,463 B2
(45) Date of Patent: Nov. 23, 2021

(54) THIAZOLE INNER SALT COMPOUNDS, AND PREPARATION METHODS AND USES THEREOF

(71) Applicant: Institute of Pharmacology and Toxicology Academy of Military Medical Sciences P.L.A. China, Beijing (CN)

(72) Inventors: Song Li, Beijing (CN); Wu Zhong, Beijing (CN); Shuang Cao, Beijing (CN); Lili Wang, Beijing (CN); Zhibing Zheng, Beijing (CN); Junhai Xiao, Beijing (CN); Xinbo Zhou, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 252 days.

(21) Appl. No.: 16/382,539

(22) Filed: Apr. 12, 2019

(65) Prior Publication Data
US 2019/0233383 A1 Aug. 1, 2019

Related U.S. Application Data

(62) Division of application No. 14/902,986, filed as application No. PCT/CN2014/081859 on Jul. 9, 2014, now abandoned.

(30) Foreign Application Priority Data

Jul. 9, 2013 (CN) .......................... 201310285490.X

(51) Int. Cl.
| | |
|---|---|
| *C07D 277/22* | (2006.01) |
| *A61K 31/426* | (2006.01) |
| *C07D 277/30* | (2006.01) |
| *A61K 8/49* | (2006.01) |
| *A61K 31/4422* | (2006.01) |
| *A61Q 11/00* | (2006.01) |
| *A61Q 19/08* | (2006.01) |

(52) U.S. Cl.
CPC .............. *C07D 277/22* (2013.01); *A61K 8/49* (2013.01); *A61K 31/426* (2013.01); *A61K 31/4422* (2013.01); *A61Q 11/00* (2013.01); *A61Q 19/08* (2013.01); *C07D 277/30* (2013.01)

(58) Field of Classification Search
None
See application file for complete search history.

(56) References Cited

U.S. PATENT DOCUMENTS

| | | | |
|---|---|---|---|
| 7,799,813 B2 | 9/2010 | Li et al. | |
| 8,338,616 B2 * | 12/2012 | Li | A61P 27/02 |
| | | | 548/204 |
| 2009/0088461 A1 | 4/2009 | Thomas et al. | |
| 2009/0227643 A1 | 9/2009 | Li et al. | |
| 2011/0178141 A1 | 7/2011 | Li et al. | |
| 2016/0137619 A1 | 5/2016 | Lit et al. | |

FOREIGN PATENT DOCUMENTS

| | | | | |
|---|---|---|---|---|
| CN | 101007789 A | 8/2007 | | |
| CN | 101684106 A | 3/2010 | | |
| JP | S6019030 A | 1/1985 | | |
| JP | 2009-524605 A | 7/2009 | | |
| JP | 2012-502929 A | 2/2012 | | |
| RU | 2444517 C2 | 3/2010 | | |
| WO | WO 2010/031248 A1 * | 3/2010 | ........... | C07D 277/22 |

OTHER PUBLICATIONS

Peddie et al., Antonie van Leeuwenhoek (2003), 83(2), pp. 175-181.*
International Search Report (ISR) for PCT/CN2014/081859; I.A. fd:Jul. 9, 2014, dated Aug. 13, 2014, State Intellectual Property Office of the P.R. China, Beijing, China.
International Preliminary Report on Patentability (IPRP) including the Written Opinion of the International Searching Authority (PCT Rule 44bis) for PCT/CN2014/081859; I.A. fd: Jul. 9, 2014, dated Jan. 12, 2016, by the International Bureau of WIPO, Geneva, Switzerland.
Peddie, BA et al., "Assessment of antimicrobial activity of hydrophilic betaines in osmotically stressed bacteria," Antonie Van Leeuwenhoek, Jan. 2003; 83(2): 175-181, Kluwer Academic Publishers, Netherlands.

(Continued)

*Primary Examiner* — Brian J Davis
(74) *Attorney, Agent, or Firm* — Sterne, Kessler, Goldstein & Fox P.L.L.C.

(57) ABSTRACT

The present invention pertains to field of pharmaceutical chemicals, and relates to thiazole inner salt compounds, preparation methods and uses thereof. Specifically, the present invention relates to a compound of Formula I, hydrates or pharmaceutically acceptable salts thereof. The compound of Formula I of the present invention is a potent cross-linking protein cleavage agent, has a stable structure, good physical and chemical properties, and good pharmacological activities, and is suitable for large scale production to obtain samples with stable, controllable and reliable quality, thereby being suitable for pharmaceutical development.

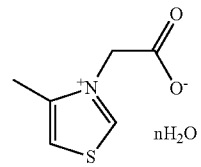

Formula I

8 Claims, 15 Drawing Sheets

(56) References Cited

OTHER PUBLICATIONS

Ikeda, H et al., "Thiamine-appended cyclodextrin dimer as a ligase model," in Proceedings of the Ninth International Symposium on Cyclodextrins, JJT Labandeira et al., eds., Santiago de Compo stela, Spain, May 31-Jun. 3, 1998, Springer Science+Business Media, Netherlands (1999) pp. 129-132.

Washabaugh, MW et al., Hydrolysis of Thiamin: Evidence for Rate-Limiting Breakdown of the Tricyclic Dihydrothiachromine Intermediate in Neutral Aqueous Solution, Bioorganic Chemistry, Jun. 1993; 21(2), 170-191, Elsevier, B.V., Amsterdam.

Office action dated Aug. 23, 2016, for CN Appl. No. 201480038496. X, from SIPO, Beijing, CN.

Cao, S et al., Novel cross-link breaker based on zwitterion structure: synthesis, structure and druggability studies, Eur J Med Chern. Oct. 2013;68:89-95. doi: 10.1016/j.ejmech.2013.07.033. Epub Aug. 9, 2013.

Extended European search report, including the supplementary European search report and the European search opinion, for EP Appl. No. 14822521.2, dated Jan. 31, 2017, European Patent Office, Munich, Germany.

Communication pursuant to Article 94(3) EPC dated Feb. 21, 2018, for EP Appl. No. 14822521.2, European Patent Office, Munich, Germany.

Hirayama et al., "Organic compound crystal production handbook-principle know-how," Maruzen Co. Ltd., p. 57-84, (Jul. 25, 2008).

Teruzo, A., et al., "Solvent Handbook," Kodansha Inc., p. 47-51 (1985).

Kagaku, N., et al., "Experimental Science Lecture," Maruzen Co. Ltd., pp. 159-162 and 184-193 (Jan. 25, 1967).

Office Action for Japanese Patent Application No. JP2016-524670, dated Apr. 17, 2018, The Japanese Patent Office, Tokyo, Japan.

Office Action for Russian Application No. RU2016104055, dated Mar. 29, 2018, The Russian Patent Office, Moscow, Russia.

Office Action for Japanese Patent Application No. JP2016-524670, dated Jul. 31, 2018, The Japanese Patent Office, Tokyo, Japan.

* cited by examiner

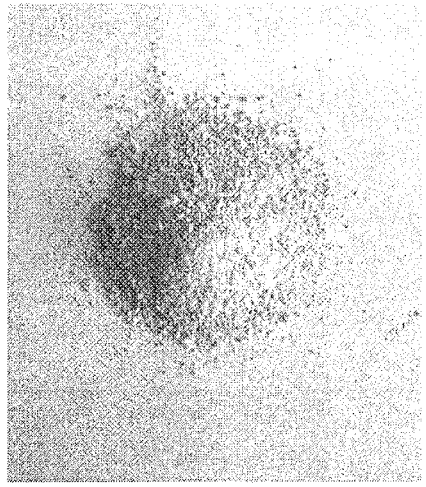 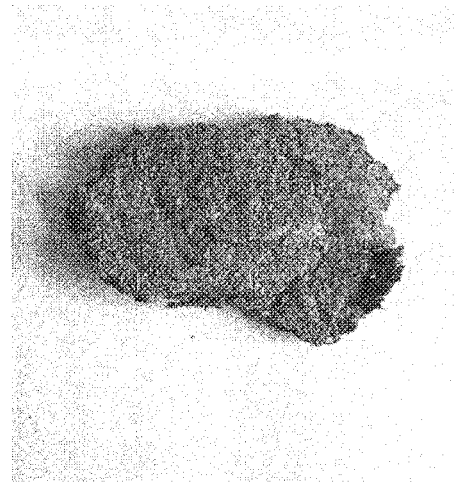
Fig.1A  Fig.1B
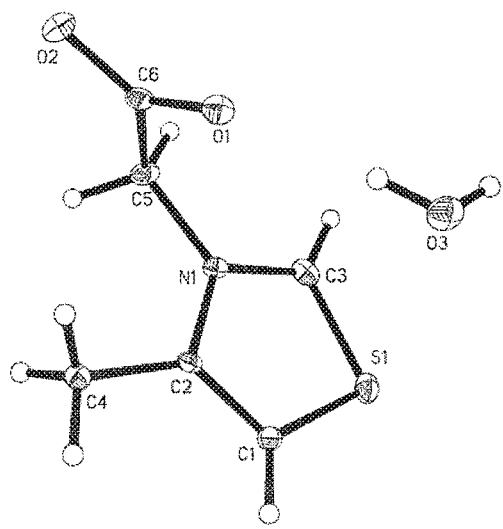
Fig.2

THIAZOLE INNER SALT COMPOUNDS, AND PREPARATION METHODS AND USES THEREOF

TECHNICAL FIELD

The present invention pertains to field of pharmaceutical chemicals, and relates to thiazole inner salt compounds, and their preparation methods and uses.

BACKGROUND ART

Advanced glycation end products (AGEs) are covalent addition products which are formed by spontaneous reaction under non-enzymatic catalysis between a macromolecule such as protein, lipoprotein or nucleic acid and a glucose or other reducing sugar in vivo in physiological environment with human aging and diabetic development. The formation of AGEs cross-linked structure is a slow procedure, in which a terminal reducing amino group of macromolecule and an aldehyde group of glucose molecule form reversible early glycation products (Schiff bases) via addition; after several days, the unstable Schiff bases gradually form more stable Amadoric type early glycation products via rearrangement reaction, and the Amadoric products form AGEs via a series of dehydrogenation, oxidation and rearrangement reactions which mechanisms are not clear enough. Due to the cross-linkability of AGEs, AGEs cross-linked structure with larger molecular weight can be formed between AGEs and macromolecules such as proteins, fats and nucleic acids via dicarbonyl bonds as bridges which are formed via glycosylation.

AGEs form cross-linked structures which make collagen aging, accelerate arteriosclerosis, change matrix components, cause platelet aggregation, result in decrease of vascular elasticity, reduction of vascular compliance and generation of abnormal lipoprotein metabolism, thereby impairing function of cardiovascular system. Hence, AGEs are closely associated with many complications of diabetes and aging processes, such as renal hypofunction, nervous system diseases, strokes, Alzheimer's disease, skin aging, retinopathy, cataract, cardiovascular diseases and arteriosclerosis.

At present, some therapeutic methods for inhibiting AGEs accumulation have been developed. Chinese Invention Patent CN101684106B discloses a thiazole onium salt compound, for example, 3-carboxylmethyl-4-methyl-thiazolium bromide of the following Formula A:

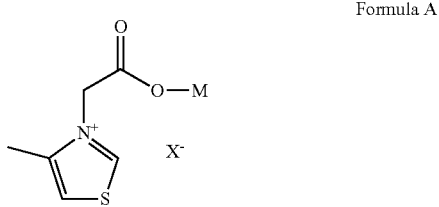

Formula A wherein:
M is Na or K;
X is Br, Cl or I;
the compound of Formula A can significantly reduce in vivo the AGEs fluorescence contents of aorta, myocardium of left ventricle and kidney in long-term diabetic rats, and in the meantime, the solubility of myocardial collagen and tail collagen could be improved, the aorta compliance of diabetic rats could be improved, the total peripheral resistance could be reduced, the cardiac output could be increased, and left ventricular function could be significantly improved. Thus, this compound can lyse the formed AGEs cross-linked structure, reconstruct vascular structure, reverse sclerosis and dysfunction induced by diabetics in cardiovascular system, and is a new type of AGEs breaker.

However, in the following researchers, the compound of Formula A is unstable in physical and chemical properties, difficult in control of product quality in large scale production process, and its sample is unstable in storage at room temperature and easy to absorb moisture and change color, so that it is not suitable to be further developed as a medicament.

For example:

(1) The results of elemental analysis of the compound of Formula A in many tests showed significant difference, and were far away from the theoretical value (exceeding 0.3 percent error limit).

(2) The quality is not stable, it is easy to absorb moisture, agglomerate and change color after storage for 3 months (temperature: 40° C., humidity: 75%, atmospheric pressure), see also: FIG. 1A and FIG. 1B.

Without being restricted by any theories, the inventors of the present invention found after carefully studying results of X-ray diffraction and elemental analysis that the compound having both quaternary ammonium salt structure and carboxylate structure is very difficult to be exist in molecular form independently and stably, in which the possible reasons could be that Na and Br in the molecule could very easily combine in NaBr form, so that the compound of Formula A has a significant defect in druggability.

The compound of Formula A shows great pharmacological activity and good pharmacokinetic properties in vitro and in vivo, but its form of onium bromide is unstable in physical and chemical properties and thus is not suitable to be used as a medicament.

Hence, it is still in need to develop a new stable and effective thiazole inner salt compound.

Contents of the Invention

The inventors of the present invention obtained a thiazole inner salt compound of Formula I upon deeply researches and creative work. The inventors surprisingly found that the compound of Formula I was stable structurally, and had excellent physical and chemical properties as well as good pharmacologic activity; and could be produced in a large scale to obtain samples with stable, controllable and reliable quality, thereby being suitable for pharmaceutical development. Hence, the following invention is provided:

One aspect of the present invention relates to a compound of Formula I or a pharmaceutically acceptable salt thereof,

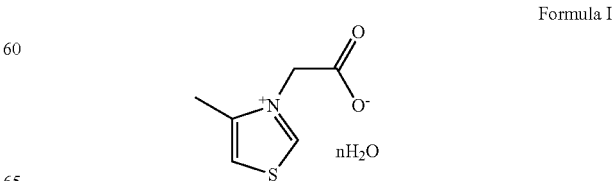

Formula I wherein:

n is 0, 1, 2 or 3.

The compound of Formula I or a pharmaceutically acceptable salt thereof according to any item of the present invention, wherein said compound of Formula I is selected from:

3-methylcarbonyloxy-4-methyl-thiazole inner salt (n=0), and 3-methylcarbonyloxy-4-methyl-thiazole inner salt monohydrate (n=1).

The 3-methylcarbonyloxy-4-methyl-thiazole inner salt can be a product obtained by direct synthesis.

The 3-methylcarbonyloxy-4-methyl-thiazole inner salt monohydrate can be a monocrystal culture product of 3-methylcarbonyloxy-4-methyl-thiazole inner salt.

The method for preparing the monocrystals (n=1, 2 or 3) of the compound of Formula I, comprises the following steps:

3-methylcarbonyloxy-4-methyl-thiazole inner salt (n=0) is dissolved in methanol, then is added with ethyl acetate drop-wisely and is left to stand to obtain monocrystals; preferably, for 1 mg of 3-methylcarbonyloxy-4-methyl-thiazole inner salt, 0.05 mL of methanol and 0.3 mL of ethyl acetate are used.

In one embodiment of the present invention, the method for preparing the monocrystal comprises: 2 mg of 3-methylcarbonyloxy-4-methyl-thiazole inner salt white crystal is provided, added with 0.1 mL of methanol, then is added with 0.6 mL of ethyl acetate after crystal is dissolved and is left to stand until crystal particles slowly grow into monocrystal.

In one embodiment of the present invention, provided is a crystal form of compound 3-methylcarbonyloxy-4-methyl-thiazole inner salt (n=0), of which X-ray powder diffraction spectrum shows characteristic diffraction peaks at 12.6, 13.3, 14.9, 18.5, 19.1, 27.0, 27.7, 28.8, 29.8, 32.1, 40.8, 42.8, 45.2, 47.9, 52.6, 54.8, 55.6, 59.0 (2θ/° C.) (see details in FIG. 4).

In one embodiment of the present invention, provided is a crystal form of compound 3-methylcarbonyloxy-4-methyl-thiazole inner salt monohydrate (n=1), of which X-ray powder diffraction spectrum shows characteristic diffraction peaks at 11.8, 15.2, 16.7, 18.9, 19.3, 19.8, 21.0, 23.8, 24.5, 25.2, 26.4, 26.9, 28.6, 29.3, 31.3, 31.9, 32.1, 34.1, 34.7, 35.0, 35.6, 38.9, 40.1, 40.6, 43.1, 45.9, 46.7, 48.1, 49.0 (2θ/° C.) (see details in FIG. 5).

Another aspect of the present invention relates to a method for preparing the compound of Formula I according to any item of the present invention, comprising the following steps:

Compound A is reacted with 1,2-epoxypropane to obtain Compound B,

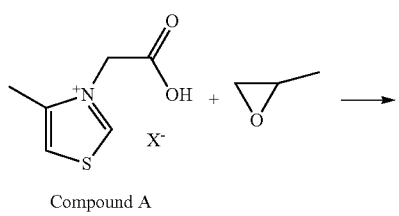

Compound A

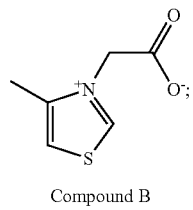

Compound B wherein, in the structure of Compound A, X is chlorine, bromine or iodine.

The method according to any item of the present invention, wherein Compound A is prepared via the following steps:

4-methylthiazole is reacted with chloroacetic acid, bromoacetic acid or iodoacetic acid to obtain Compound A,

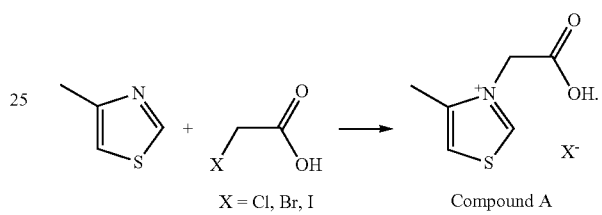

X = Cl, Br, I            Compound A

The Compound B is 3-methylcarbonyloxy-4-methyl-thiazole inner salt (n=0).

The method according to any item of the present invention, in which Compound A and/or Compound B is separated and purified via recrystallization; preferably, the solvent used for recrystallization is any one independently selected from the group consisting of acetone, methanol, ethanol, ethyl ether, petroleum ether, and n-hexane, or any mixture thereof.

In one embodiment of the present invention, the preparation method comprises: dissolving 15.6 g 4-methylthiazole in 50 mL of anhydrous acetone, adding with 21 g of bromoacetic acid, stirring for 3 h, filtering to obtain a solid, recrystallizing the solid with ethanol to obtain a white solid, drying to obtain 26 g of product in yield of 72%. 10 g of 3-carboxymethyl-4-methyl-thiazolium bromide white solid is dissolved in 50 mL of distilled water, then added with 7.31 g of 1,2-epoxypropane, stirred at room temperature for 12 h; after the end of reaction, the reaction solution is extracted with 30 mL of dichloromethane, and is extracted for 3 times, wherein the dichloromethane layer is discarded; the water layer is evaporated under a reduced pressure to obtain a pale yellow oily substance. The oily substance is added with a suitable amount of acetone to precipitate pale yellow particles; the particles were recrystallized with ethanol-ethyl ether system (wherein the optimized recrystallization ratio is as following: 1 g of yellow particles is dissolved in 4.5 mL of ethanol under heating, then added with 2 mL of ethyl ether) to obtain 5.15 g of white crystal in a yield of 78%.

In one embodiment of the present invention, the preparation method comprises:

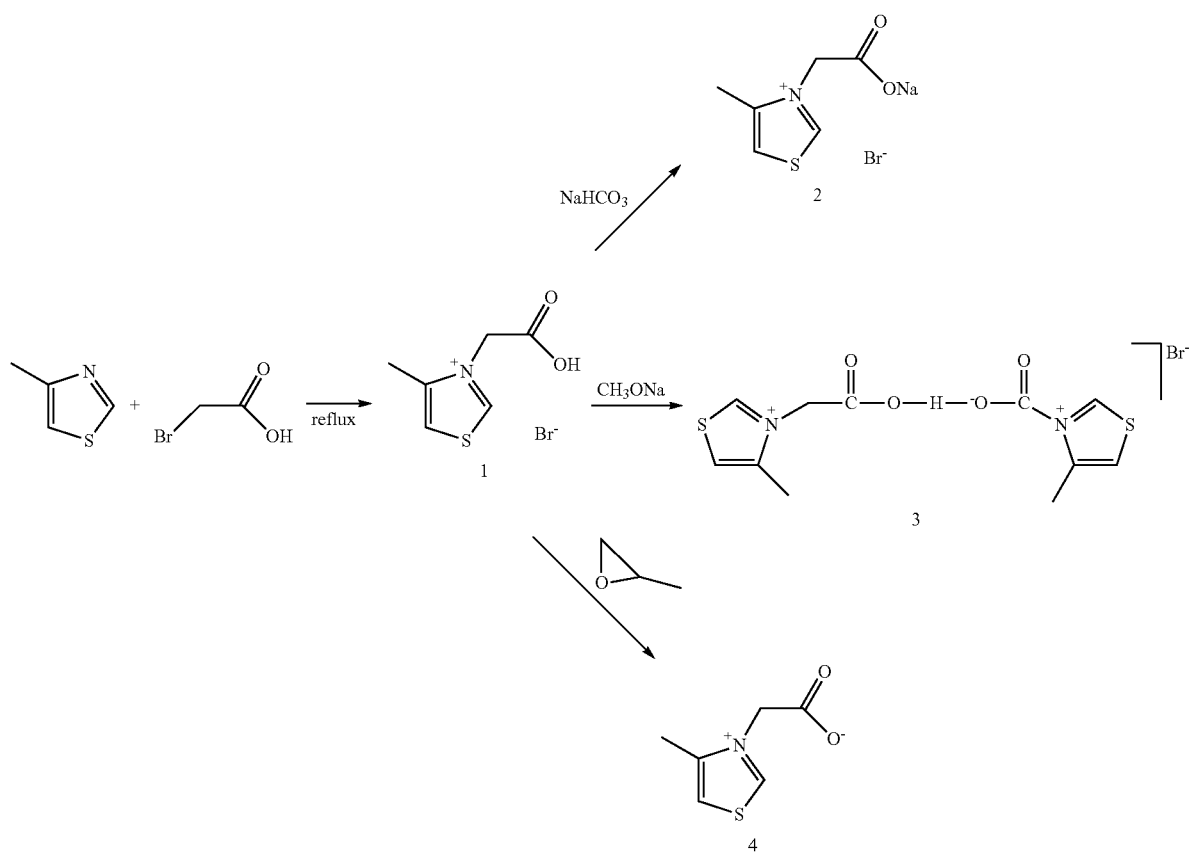

The inventors obtained Compound 3 and Compound 4 (FIG. 2) via a plenty of creative synthesis designs and practical explorations, tested the chemical properties and in vivo pharmacokinetic properties of these two compounds, and finally determined that the zwitterion compound 4 (3-methylcarbonyloxy-4-methyl-thiazole inner salt, $CH_7NO_2S$) is the most stable form of this structure.

Further another aspect of the present invention relates to a composition, comprising one or more of the compounds of Formula I or the pharmaceutically acceptable salt thereof according to any item of the present invention, and optionally one or more pharmaceutically or cosmetically acceptable excipients; optionally, the composition further comprises one or more antihypertensive drugs; preferably, said antihypertensive drug is Nifedipine; preferably, said composition is an oral cavity cleaning preparation.

In one embodiment of the present invention, the composition is a pharmaceutical composition. The pharmaceutical composition can be in various forms for different administration routes.

The pharmaceutical composition of the present invention comprises an effective amount of compound of Formula I, its hydrate or pharmaceutically acceptable salt as well as one or more suitable pharmaceutically acceptable carriers. The pharmaceutically acceptable carriers include but are not limited to: ion exchangers, aluminum oxide, aluminum stearate, lecithin, serum protein such as human serum albumin, buffer substance such as phosphate, glycerin, sorbic acid, potassium sorbate, mixture of partial glycerides of saturated vegetable fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, celluloses, polyethylene glycol, sodium carboxyl methylcellulose, polyacrylates, bee wax, wool grease.

The compounds of the present invention are a group of potent cross-linked proteins breakers, have excellent ability of breaking glycosylated aged proteins, and thus can be used for, but not limited to, (i) increasing skin elasticity or reducing skin wrinkle; (ii) treating diabetics; (iii) treating or relieving sequelae of diabetics; (iv) treating or relieving kidney injury; (v) treating or relieving vascular injury; (vi) treating or relieving hypertension; (vii) treating or relieving retinopathy; (viii) treating or relieving lensprotein injury; (ix) treating or relieving cataract; (x) treating or relieving peripheral neuropathy; (xi) treating or relieving osteoarthritis; (xii) being used in combination with antihypertensive agent for treating diabetes-associated hypertension.

The compounds of the present invention can significantly improve sclerosis of cardiovascular system.

The compounds of the present invention can well enhance therapeutic sensitivity of diabetes or cardiovascular to drugs.

The compounds of the present invention have effects of treating chronic heart failure.

Non-enzymatic reactions in oral cavity may result in tooth staining. The currently used anticarious agents may accelerate carbonylation and further result in tooth staining. Recently, a kind of cationic bactericides with anticarious function is commonly used for conventional oral cavity cleaning. These cationic antibacterial agents include Alexidine, cetylpyridinium chlorate, etc. These agents can accelerate the critical Maillard reaction in glycosylation, thereby accelerating tooth staining (Nordbo, J. Dent. Res., 58:1429 (1979)). In addition, some reports showed in vitro that hibitane and zephiran can catalyze glycosylation (Browning Reaction). Due to the Maillard reaction, the addition of hibitane into the mixture of sugar and amino acid accelerate the formation of pigments.

Based on the above mechanism, the compounds and their pharmaceutical compositions of the present invention can be used in oral cavity, especially used as an oral cavity cleaning solution and an additive in toothpaste.

For the above uses of the compounds of the present invention, suitable forms of nontoxic and pharmaceutically acceptable carriers can be used in mouth cleaning solutions and toothpastes.

The pharmaceutical composition of the compounds of the present invention can be administrated in any one of the following routines: oral administration, spray inhalation, rectal application, nasal administration, buccal administration, local administration, parenteral administration, such as subcutaneous, intravenous, intramuscular, intraperitoneal, intrathecal, intraventricular, intrasternal and intracranial injection or infusion, or administration via an explanation reservoir, in which oral administration, intraperitoneal or intravenous administration are preferably.

As for oral administration, the compounds of the present invention can be in any orally acceptable preparation forms, including but not being limited to tablets, capsules, water solutions or water suspensions, in which the carriers used for tablets usually comprise lactose and corn starch, and lubricant such as magnesium stearate can be further added. The diluents used for capsule preparations usually include lactose and dry corn starch. In water suspensions, the active ingredient is usually used in mixing with emulsifying agent and suspending agent. If necessary, the above oral preparation may further comprise sweetening agent, flavoring agent or coloring agent.

For local administration, especially local external application, to suffering surfaces or organs such as eyes, skin or lower intestinal tract, the compounds of the present invention can be in different local administration forms for different suffering surfaces or organs. The details are as follows.

For local administration to eyes, the compounds of the present invention can be in preparation forms of micronization suspensions or solutions, in which the used carriers can be isotonic sterile saline with certain pH value, and preservative such as chlorobenzylalkoxide can be added or not. For eye uses, the compounds may also be in paste form such as Vaseline paste.

For local administration to skin, the compounds of the present invention can be in form of suitable ointment, lotion or cream, in which the active ingredients are suspended or dissolved in one or more carriers. The carriers used in ointment include but are not limited to mineral oil, liquid Vaseline, white Vaseline, propylene glycol, polyoxyethylene, polyoxypropylene, emulsifying wax and water; the carries used in lotion or cream include but are not limited to mineral oil, sorbitan monostearate, Tween-60, hexadecane ester wax, hexadecane aromatic alcohol, 2-octyldodecyl alcohol, benzyl alcohol and water.

The compounds of the present invention can also be administrated in form of sterile injections, comprising sterile injection water or oily suspending liquid or sterile injection solution, in which the usable carriers and solvents include water, Ringer's solution or isotonic sodium chloride solution. In addition, sterilized nonvolatile oil such as monoglyceride or diglyceride may also be used as solvent or suspending medium.

Further another aspect of the present invention relates to a use of the compound of Formula I or the pharmaceutically acceptable salt thereof according to any item of the present invention in manufacture of a product such as a medicament for treatment and/or relief and/or prophylaxis and/or adjuvant therapy of protein aging associated disease or disorder; preferably, said protein aging associated disease or disorder are one or more selected from:

i) skin elasticity decrease or skin wrinkles increase; ii) diabetes; iii) sequelae of diabetes; iv) kidney injury; v) vascular injury; vi) hypertension; vii) retinopathy; viii) lensprotein injury; ix) cataract; x) peripheral neuropathy; xi) osteoarthritis; xii) diabetes associated hypertension.

Further another aspect of the present invention relates to a use of the compound of Formula I or the pharmaceutically acceptable salt thereof according to any item of the present invention in manufacture of a reversal agent for tooth-staining in an animal; an oral preparation for preventing or reversing tooth-staining; a protein preservative or an animal protein preservative; a breaker for cross-linked protein, a medicament for breaking advanced glycation end products; a medicament for reducing plasma BNP content and/or plasma MCP-1 content; a medicament for improving cardiovascular system sclerosis; a medicament for enhancing therapeutic sensitivity for diabetes and cardiovascular disease; or a medicament for treatment and/or prophylaxis and/or adjuvant therapy of chronic heart failure.

Further another aspect of the present invention relates to a method selected from any one of the following items (1)-(7), characterized in that the method comprises a step of using or administering an effective amount of the compound of Formula I or the pharmaceutically acceptable salt thereof according to any item of the present invention, or the composition according to the present invention:

(1) a method for breaking advanced glycation end products (AGEs) in vivo or in vitro;

(2) a method for improving cardiovascular system sclerosis;

(3) a method for enhancing sensitivity of diabetes or cardiovascular disease for drug therapy;

(4) a method for treatment and/or prophylaxis and/or adjuvant therapy of chronic heart failure;

(5) a method for preventing or reversing tooth-staining;

(6) a method for preservation of plant protein or animal protein;

(7) a method for treatment and/or relief and/or prophylaxis and/or adjuvant therapy of protein aging associated disease or disorder; preferably, said protein aging associated disease or disorder is selected from:

i) skin elasticity decrease or skin wrinkles increase; ii) diabetes; iii) sequelae of diabetes; iv) kidney injury; v) vascular injury; vi) hypertension; vii) retinopathy; viii) lensprotein injury; ix) cataract; x) peripheral neuropathy; xi) osteoarthritis; xii) diabetes associated hypertension.

In one embodiment of the present invention, the methods are not aimed at therapy.

It should be pointed out that the dose and method of using the compound of the present invention depend on many factors, including ages, bodyweights, genders, general physical conditions and nutritional status of patients, activity intensity of compounds, administration time, metabolic rate, severity of disorders and subjective judgment of attending physicians. The preferable dose is between 0.01 to 100 mg/kg (bodyweight)/day, in which the most preferable dose is 20 mg/kg to 30 mg/kg (bodyweight)/day.

In the present invention, the term "effective amount" refers to a dose that can fulfill treatment, prophylaxis, alleviation and/or relief of the disease or disorder described in the present invention in a subject.

The term "subject" refers to a patient or an animal, such as human, dog, monkey, bovine, equine, that is administered with the composition of the present invention for treatment, prophylaxis, alleviation and/or relief of the disease or disorder of the present invention.

The term "disease and/or disorder" refers to a physical state of a subject, which is related to the disease and/or disorder of the present invention.

Beneficial Effects of the Present Invention

The compound of Formula I, its hydrate or pharmaceutically acceptable salt has equivalent activity for breaking AGEs and more stable pharmacokinetics in comparison with the preferable compound 3-carboxymethyl-4metyl-bromothiazolium sodium salt (see: Formula A) disclosed in CN101684106B; in addition, the product is easier in quality control and more suitable for pharmaceutical industry and/or cosmetic industry.

BRIEF DESCRIPTION OF THE DRAWINGS

FIG. 1: comparison of appearances of the compound of Formula A (M=Na, K=Br) before and after three months of storage, in which FIG. 1A is of the newly prepared compound of Formula A; FIG. 1B is of the compound of Formula A after three months of storage (temperature: 40° C., humidity: 75%, atmospheric pressure).

FIG. 2: the X-single crystal diffraction structure diagram of 3-methylcarbonyloxy-4-methyl-thiazole inner salt monohydrate (n=1).

SPECIFIC MODELS FOR CARRYING OUT THE PRESENT INVENTION

The embodiments of the present invention are described in details in conjunction with the following examples, but those skilled in the art would understand the examples are used for illustrating the present invention only, rather than for limiting the scope of the present invention. Any specific conditions that were not given in the examples are conventional conditions or conditions suggested by the manufacturers. The reagents or instruments which manufacturers were not given were all conventional products commercially available in markets.

Melting points of compounds were measured with SRY-1 type melting point apparatus, which was not subjected to temperature calibration. 1H-NMR and 13C-NMR spectra were measured with BrukerARX400 type nuclear magnetic resonance spectrometer; mass spectra were measured with API-150EX LC/MS high resolution mass spectrometer; X-ray single crystal diffraction was measured with Rigaku Saturn944 CCD diffractometer; X-ray powder diffraction was measured with Bruker D8 Advance diffractometer.

Example 1: Preparation of 3-carboxymethyl-4-methyl-thiazolium bromide (Compound A)

15.6 g 4-methylthiazole was dissolved in 50 mL anhydrous acetone, added with 21 g bromoacetic acid, stirred for 3 h, filtered to obtain a solid, recrystallized with ethanol to obtain a white solid, dried to obtain 26 g of product, yield 72%, mP=240.6-241.6° C.

MS[M]$^+$=158.2 m/e; $^1$H-NMR (400 MHz, DMSO-d$_6$), 2.48 (d, 3H); 5.55 (s, 2H); 8.09 (d, 1H); 10.25 (d, 1H); 14.05 (brs, H).

Example 2: Preparation of 3-methylcarbonyloxy-4-methyl-thiazole Inner Salt (n=0)

10 g 3-carboxymethyl-4-methyl-thiazolium bromide white solid was dissolved in 50 mL distilled water, added then with 7.31 g 1,2-epoxypropane, stirred at room temperature for 12 h, after the end of reaction, the reaction solution was extracted with 30 mL of dichloromethane, for 3 times, dichloromethane layer was discarded; the water layer was evaporated at a reduced pressure to obtain a light yellow oily substance. A defined amount of acetone was added into the oily substance, and light yellow particles were obtained via precipitation; recrystallization was performed with ethanol-ethyl ether system (wherein the most preferable recrystallization ratio was: 1 g of yellow particles was heated and dissolved in 4.5 mL ethanol, then added with 2 mL ethyl ether), to obtain white crystal 5.15 g, yield 78%, mP=169° C.

MS: 158 [M+H]$^+$, 315 [2M+H]$^+$, 472 [3M+H]$^+$; $^1$H-NMR (400 MHz, DMSO-d$_6$), 2.41 (d, 3H), 4.76 (s, 2H), 7.90 (d, 1H), 9.97 (d, 1H); $^{13}$C-NMR (Methanol-d$_4$), δ 12.98, 56.71, 121.47, 148.36, 169.71;

Elemental analysis: Anal. Calcd for C$_6$H$_7$NO$_2$S (157.2): C, 45.85; H, 4.49; N, 8.91%

Found: C, 45.74; H, 4.51; N, 8.87%.

The crystal structure was measured with X-single crystal diffraction.

Figure 4:
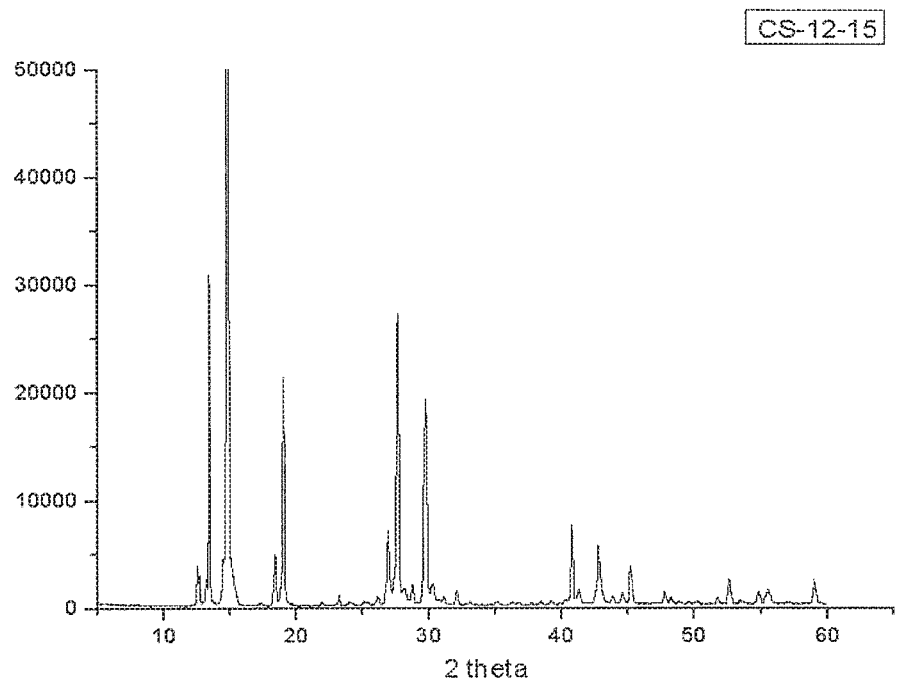
FIG. 4: the X-ray powder diffraction diagram of 3-methylcarbonyloxy-4-methyl-thiazole inner salt (n=0).

It was a crystal form compound 3-methylcarbonyloxy-4-methyl-thiazole inner salt (n=0), and its X-ray powder diffraction spectra showed characteristic diffraction peaks at 12.6, 13.3, 14.9, 18.5, 19.1, 27.0, 27.7, 28.8, 29.8, 32.1, 40.8, 42.8, 45.2, 47.9, 52.6, 54.8, 55.6, 59.0 (2θ/° C.) (see details in FIG. 4).

Example 3: Preparation of 3-methylcarbonyloxy-4-methyl-thiazole Inner Salt Monohydrate (n=1)

2 g of the 3-methylcarbonyloxy-4-methyl-thiazole inner salt (n=0) as prepared in Example 2 was dissolved at 20° C. in a mixture solvent of 100 mL methanol and 1 mL water, after complete dissolution, 300 mL ethyl acetate solution was added slowly; after mixing homogeneously, standing was performed at 5° C. for 12 h, the precipitated crystal was 3-methylcarbonyloxy-4-methyl-thiazole inner salt monohydrate (n=1).

Test of crystal structure determination with X-ray single crystal diffraction:

2 mg of 3-methylcarbonyloxy-4-methyl-thiazole inner salt white crystal was added with 0.1 mL of anhydrous methanol, after the particles were dissolved, 0.6 mL ethyl acetate was added drop-wisely, standing was carried out until crystal particles grew slowly to form monocrystals (3-methylcarbonyloxy-4-methyl-thiazole inner salt monohydrate, n=1). Crystal structure was determined with X-single crystal diffraction.

Figure 5:
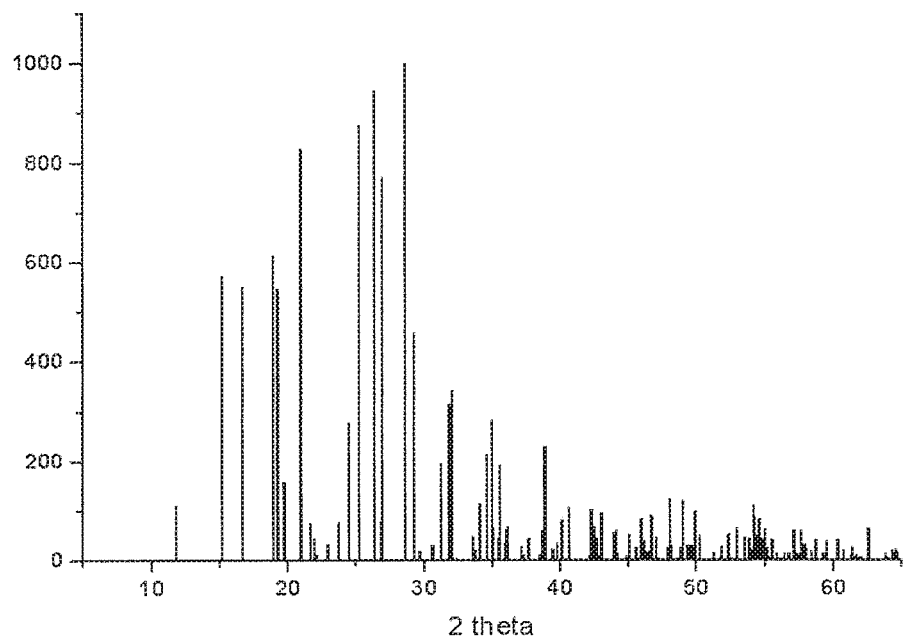
FIG. 5: the X-ray powder diffraction diagram of 3-methylcarbonyloxy-4-methyl-thiazole inner salt monohydrate (n=1).

It was a crystal form of the compound 3-methylcarbonyloxy-4-methyl-thiazole inner salt monohydrate (n=1), and its X-ray powder diffraction spectra showed characteristic diffraction peaks at 11.8, 15.2, 16.7, 18.9, 19.3, 19.8, 21.0, 23.8, 24.5, 25.2, 26.4, 26.9, 28.6, 29.3, 31.3, 31.9, 32.1, 34.1, 34.7, 35.0, 35.6, 38.9, 40.1, 40.6, 43.1, 45.9, 46.7, 48.1, 49.0 (2θ/° C.). (see details in FIG. 5).

Crystallographic data: C$_6$H$_7$NO$_2$S.H$_2$O, Mr=175.20, orthorhombic system, space group P-1, crystallographic parameters: a=5.6082(11) Å, alpha=90 deg., b=8.4615(17) Å, beta=90 deg., c=16.064(3) Å, gamma=90 deg.

Figure 3:
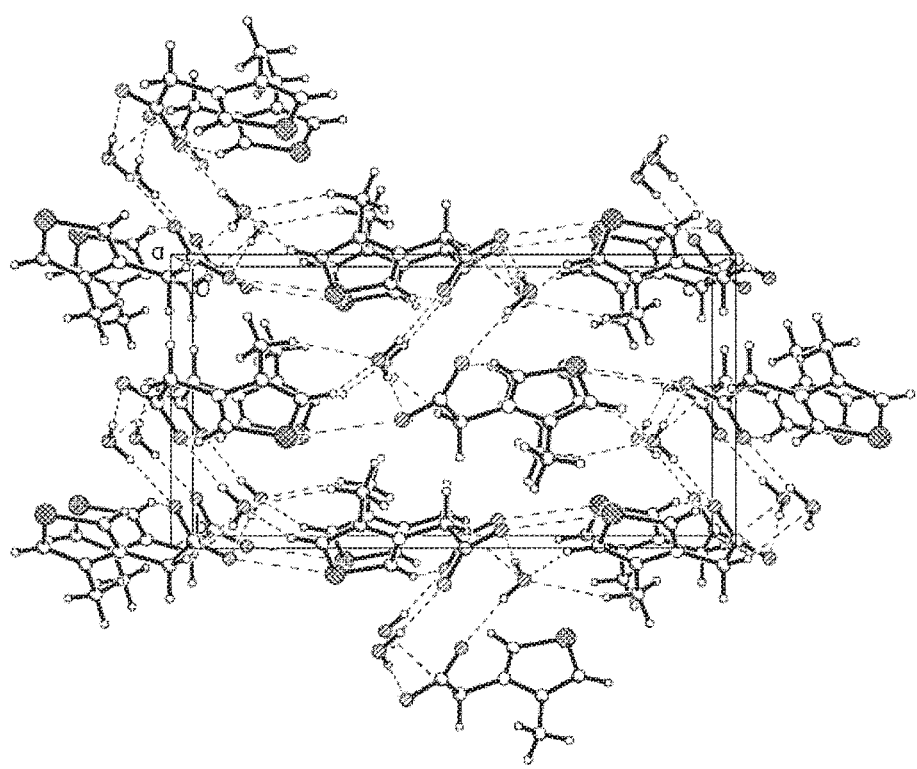
FIG. 3: the molecular crystal packing diagram of 3-methylcarbonyloxy-4-methyl-thiazole inner salt monohydrate (n=1).

The single crystal structure diagram was shown in FIG. 2. Molecular crystal packing diagram was shown in FIG. 3.

Example 4: Stability Test

Three batches of sample (prepared according to Example 2) were taken according to the Chinese Pharmacopoeia, 2010 Edition, packaged like packaging for sale (high-density polyethylene bags were used for drug packaging), placed under conditions of RT40° C., RH75% (NaCl saturated solution) to carry out accelerated test, after 1, 2, 3, 6 months, sampled for observation of the compound of Formula I and the compound of Formula A, compared to the data of the 0$^{th}$ day, and the results were shown in Table 1 and Table 2.

One batches of sample as prepared according to Example 3 were taken, packaged like packaging for sale (high-density polyethylene bags were used for drug packaging), placed under conditions of RT40° C., RH75% (NaCl saturated solution), after 1, 2, 3 months, sampled and compared to the data of the 0$^{th}$ day, and the results were shown in Table 3.

Three batches of sample of the compound of Formula A were taken according to the Chinese Pharmacopoeia, 2010 Edition, packaged like packaging for sale (high-density polyethylene bags were used for drug packaging), placed under conditions of RT40° C., RH75% (NaCl saturated solution), after 1, 2, 3 months, sampled and compared to the data of the 0$^{th}$ day, and the results were shown in Table 1 and Table 4.

TABLE 1

Comparison of quality stabilization between the compound of Formula I
(n = 0) as prepared in Example 2 to the compound of Formula A (M = Na, K = Br)

| Name of compound | Elemental analysis | Accelerated test, 3 months |
|---|---|---|
| Compound of Formula I (n = 0) | C: 45.72, H: 4.51, N: 8.87%. (standard values: C: 45.85, H: 4.49, N: 8.91%) | no obvious appearance change |
|  | C: 45.75, H: 4.52, N: 8.88% | no obvious appearance change |
|  | C: 45.83, H: 4.52, N: 8.92%. | no obvious appearance change |

TABLE 1-continued

Comparison of quality stabilization between the compound of Formula I
(n = 0) as prepared in Example 2 to the compound of Formula A (M = Na, K = Br)

| Name of compound | Elemental analysis | Accelerated test, 3 months |
|---|---|---|
| Compound of Formula A (M = Na, K = Br) 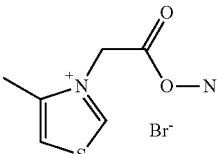 | C: 30.79, H: 2.78, N: 5.46, Br: 27.63%. (standard values: C: 27.71, H: 2.71, N: 5.39, Br: 30.72%) | caking, appearance changing into dark brown |
| | C: 29.57, H: 2.80, N: 5.50, Br: 28.30%. | caking, appearance changing into dark brown |
| | C: 29.09, H: 2.68, N: 5.45, Br: 28.68%. | caking, appearance changing into dark brown |

TABLE 2

Purity observation results of the compound of Formula
I as prepared in Example 2 in the accelerated tests

| Batch | Time | Appearance and color | Purity* (%) | Melting point (° C.) | Weight gain (%) |
|---|---|---|---|---|---|
| 1 | 0th month | faint yellow to yellow powder | 99.8 | 168.3-169.8 | 0 |
| | 1st month | faint yellow to yellow powder | 99.7 | 168.1-169.7 | 0.11 |
| | 2nd month | faint yellow to yellow powder | 99.6 | 168.2-169.9 | 0.12 |
| | 3rd month | faint yellow to yellow powder | 99.8 | 168.2-169.8 | 0.15 |
| | 6th month | faint yellow to yellow powder | 99.9 | 168.1-169.9 | 0.18 |
| 2 | 0th month | faint yellow to yellow powder | 100.0 | 168.4-170.2 | 0 |
| | 1st month | faint yellow to yellow powder | 99.8 | 168.3-169.8 | 0.12 |
| | 2nd month | faint yellow to yellow powder | 99.2 | 168.4-169.9 | 0.12 |
| | 3rd month | faint yellow to yellow powder | 99.8 | 168.2-170.0 | 0.14 |
| | 6th month | faint yellow to yellow powder | 99.6 | 168.3-169.9 | 0.15 |
| 3 | 0th month | faint yellow to yellow powder | 99.6 | 168.3-169.9 | 0 |
| | 1st month | faint yellow to yellow powder | 99.8 | 168.4-169.9 | 0.11 |
| | 2nd month | faint yellow to yellow powder | 99.6 | 168.3-170.0 | 0.13 |
| | 3rd month | faint yellow to yellow powder | 99.3 | 168.3-170.2 | 0.13 |
| | 6th month | faint yellow to yellow powder | 99.8 | 168.2-170.1 | 0.15 |

TABLE 3

Purity observation results of the compound
of Example 3 in accelerated test

| Batch | Time | Appearance and color | Purity* (%) | Melting point (° C.) | Weight gain (%) |
|---|---|---|---|---|---|
| 1 | 0th month | faint yellow to yellow powder | 99.9 | 172.3-171.8 | 0 |
| | 1st month | faint yellow to yellow powder | 99.8 | 172.1-171.7 | 0.04 |
| | 2nd month | faint yellow to yellow powder | 99.7 | 172.2-171.9 | 0.06 |
| | 3rd month | faint yellow to yellow powder | 99.7 | 172.2-171.8 | 0.07 |

TABLE 4

Purity observation results of the compound of Formula A
(M = Na, K = Br) in the accelerated test

| Batch | Time | Appearance and color | Purity* (%) | Melting point (° C.) | Weight gain (%) |
|---|---|---|---|---|---|
| 1 | 0th month | faint yellow to yellow powder | 98.7 | >220.0 | 0 |
| | 1st month | brown, tacky | 85.1 | unmeasured | 18.0 |
| | 2nd month | dark brown, caking | 60.6 | unmeasured | 32.6 |
| | 3rd month | dark brown, caking | 51.2 | unmeasured | 41.5 |
| 2 | 0th month | faint yellow to yellow powder | 98.8 | >220.0 | 0 |
| | 1st month | brown, tacky | 82.7 | unmeasured | 18.5 |
| | 2nd month | dark brown, caking | 59.8 | unmeasured | 33.6 |
| | 3rd month | dark brown, caking | 48.5 | unmeasured | 42.1 |
| 3 | 0th month | faint yellow to yellow powder | 99.1 | >220.0 | 0 |
| | 1st month | brown, tacky | 81.6 | unmeasured | 19.0 |
| | 2nd month | dark brown, caking | 60.3 | unmeasured | 33.8 |
| | 3rd month | dark brown, caking | 54.6 | unmeasured | 44.0 |

It can be seen in the above data that the compounds of Examples 2 and Example 3 showed stabilization significantly superior to that of the known compound of Formula A, and thus had better potential to be medicament.

Example 5: Test of In Vitro Breaking Erythrocytic
Surface Cross-Linked IgG (Immune Globulin G)

Because erythrocytic surface cross-linked IgG is a typical AGEs cross-linked structure, the determination of degree that a compound breaks erythrocytic surface cross-linked IgG is well known as a better method for evaluating the ability of the compound in breaking AGEs cross-linked structure (Bruceh. R. Wolffenbuttel, Breakers of advanced glycation end products restore large artery properties in experimental diabetes, Natl. Acad. Sci. U.S.A 1998, 95, 4630).

Method for treating blood cells: 16 weeks diabetic rats were narcotized, blood samples were got from their carotid arteries, added with heparin for anticoagulation, centrifuged at 4° C. and 1000 g for 3 min, the lower layer RBC (red blood cells) was taken; washed with 0.1 mol/L PBS (pH7.4) for 3 times, centrifuged each time at 4° C. and 1000 g for 3 min; and the lower layer RBC was used for test.

In vitro administration method: 0.1 mol/L isotonic PBS (phosphate buffer) (pH7.4) was used as negative control, each of the compounds to be tested formed solutions with different concentrations using the buffer. Into per 900 μL of solution or solvent, 100 μL RBC was added, slightly shook at 37° C. for 16-18 h; centrifuged at 1000 g, 4° C. for 3 min, the supernatant was discarded, the plate was washed with 0.1 mol/L PBS (pH7.4) for 4 times to remove residual compound; centrifuged at 1000 g, 4° C. for 3 min, the lower layer RBC was diluted in ratio of 1:100 for ELISA determination.

Procedure for determination of RBC surface cross-linked IgG content via immunoadsorption method: Multiscreen-HA 0.45 μm 96-well plate (Millipore), sealed with Superblock (300 μL/well), 37° C., 1 h; then drained under 5 mmHg of negative pressure, the whole plate was washed with PBST for 3 times, washed with 0.1M PBS (pH7.4) for twice, shaking plate each time for 1 min; added with RBC (50 μL/well) to be tested, another PBS background control well ($OD_0$) was set; drained under negative pressure; washed with 150 μL of 0.1 mol/L PBS (pH7.4) for 4 times, shaking plate each time for 1 min. After being drained under negative pressure, the 1:500 diluted goat-anti-mouse IgG-HRP (50 μL/well) was added, stood at room temperature for 2 h, drained; washed with 0.1 mol/L PBS (pH7.4), 150 μL/well, for 3 times, shaking plate each time for 1 min; drained; added with o-phenylenediamine (OPD) substrate developing solution (100 μL/well), stood at room temperature in dark for 30 min, the reaction was terminated with 2 mol/L $H_2SO_4$ (100 μL/well); the reaction solution (150 μL/well) was sucked out quickly and transferred to a normal 96-well ELISA plate, and OD values were determined under 490 nm.

Calculation of Lytic Rates of the Compounds to be Tested:

Corrected OD=Average OD of RBC sample to be tested–Average OD of RBC-free PBS background well, the lytic rate is expressed in percentage of decrease of $OD_{490}$ nm value: ($OD_{490}$ nm of PBS well–$OD_{490nm}$ of compound to be tested)/$OD_{490nm}$ of PBS well×100%. The test results were shown in Table 5:

TABLE 5

Lytic rates of RBC surface cross-linked IgG caused by the compound of Example 2

| Compound | Lytic rate (decrease of OD value, %) | | | |
| --- | --- | --- | --- | --- |
| | 1 μM | 10 μM | 30 μM | 100 μM |
| Compound of Example 2 | 27.1 ± 2.2 | 27.5 ± 2.9 | 23.2 ± 5.1 | 27.9 ± 3.0 |

The results of Table 5 shows that the compound of Example 2 has high lytic rate to RBC surface cross-linked IgG.

Example 6: Effects of the Compound of Example 2 on 24 h Urine Volume/Water Intake in Rats with Diabetes Accompanied by Hypertension 1. Test Method:
   (1) Grouping and Administration Method Rats were grouped according to bodyweight and blood pressure: group of rats with diabetes accompanied by hypertension that were not administered with a drug (model group), Nifedipine group, Example 2 compound+Nifedipine group. In the meantime, pure diabetes group and normal control group of the same week-age were also set. The compound of Example 2 (36 mg/kg) was dissolved in distilled water just before use, administered intragastrically, once per day, for 5 weeks. After 3 weeks of administration, an implant was embedded in abdominal aorta, restored for week, blood pressure was monitored for 3 days, until the blood pressure become stable, then Nifedipine (0.75 mg/kg) was intragastrically administered at 10:00 am, once per day, for consecutive 7 days.

(2) Preparation of Nifedipine Solution

Nifedipine powder was placed in 5 mL EP tube, added with a defined amount of CMC-Na, added with 4 steel balls, eddied for 5-10 min, after Nifedipine was completely suspended, volume was metered, and suspension was performed again.

(3) Determination of Water-Intake and Urine Volume

In the third week of administration, the rats of each group were solely placed and fed in metabolism cage, and the water intake and urine volume within 24 hours on the $19^{th}$, $20^{th}$ and $21^{st}$ day were recorded.

(4) Blood Pressure Monitoring of the Compound of Example 2 in Combination with Nifedipine The operation procedures were the same of (1), (2), (3), after 1 week of postoperative recovery, the rat cages were placed on DSI receiver, the parameters to be monitored and channels were set, the implants were turned on by using magnetic switches; after debugging, recording biological signals was started; after consecutive 3 days, Nifedipine and the compound of Example 2 were administered at 10:00 am per day, the cardiovascular parameters of rats during time period of 10:00-20:00 were dynamically recorded, for consecutive 7 days (in this period, the saline concentration was strictly controlled at 1%).

(5) Method for Content Determination of Vasoactive Substances in Rats

Method for determination of $TXB_2$, 6-Keto-PGF1a: whole blood samples were taken, added with 40 μL of Indometacin EDTA-Na for anticoagulation, centrifuged at 4° C., 3500 rmp/min, 15 min, to obtain plasma, stored at −70° C. The determination was carried out via radioimmunoassy by Beijing Huaying Biotechnology Co., Ltd.

Method for determination of BNP, MCP-1: whole blood samples were taken, added with 40 μL EDTA-Na for anticoagulation, centrifuged at 1000 g/min, 10 min, to separate plasma, stored at −70° C. The determination was carried out via radioimmunoassy by Beijing Huaying Biotechnology Co., Ltd.

(6) Statistical Method

The test data were expressed in form of mean±SD (mean±standard deviation), SPSS2.0 software was used for processing data, statistical treatment was performed by using one-way analysis of variance, and significant difference was determined when P<0.01.

In the $3^{rd}$ week of administering the compound of Example 2, $V_{urine}/V_{water-intake}$ values of rats in 24 hours were calculated.

2. Test Results

The results were shown in Table 6:

TABLE 6

Measurement results of water-intakes and urine volumes in different groups (Mean ± SD, n = 12)

| | Model | Compound of Example 2 |
|---|---|---|
| $V_{water-intake}$ (mL) | 369.3 ± 122.7 | 375.0 ± 123.6 |
| $V_{urine}$ (mL) | 302.9 ± 101.8 | 318.3 ± 106.0 |
| $V_{urine}$/bodyweight (mL/g) | 0.82 ± 0.31 | 0.88 ± 0.31 |
| $V_{urine}$/bodyweight (mL/g) | 1.00 ± 0.78 | 1.03 ± 0.34 |
| $V_{urine}/V_{water-intake}$ | 0.79 ± 0.06 | 0.86 ± 0.05* |

*P < 0.01 vs. model.

The test results of Example 6 shows that the compound of Example 2 is capable of significantly increasing water-intake and urine volume in rats.

Figure 6:
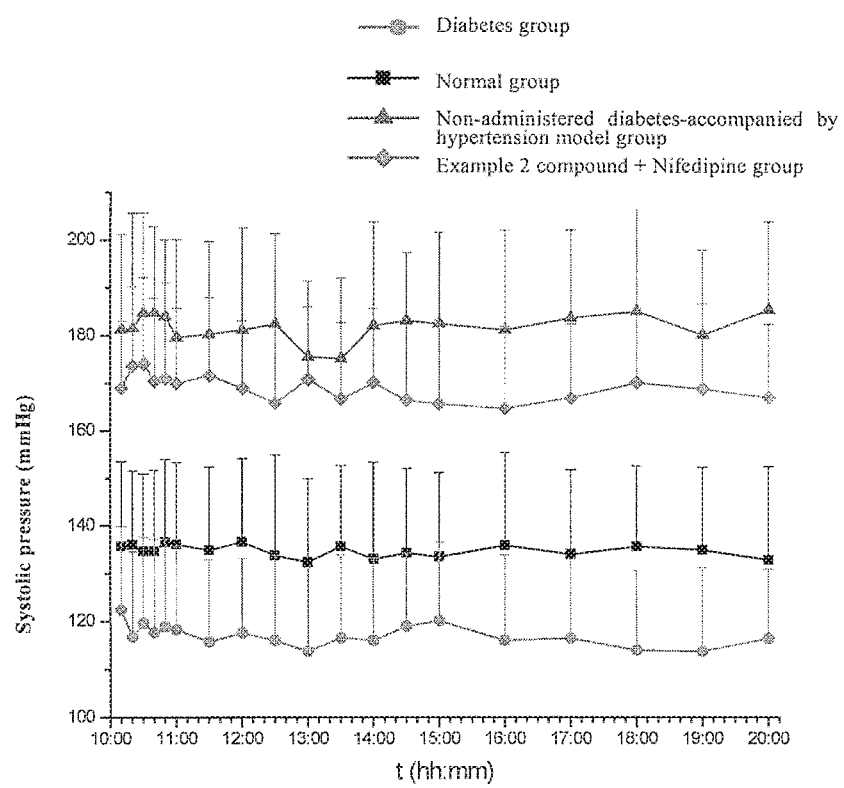
FIG. 6: systolic pressure dynamic curves of different groups during time period 10:00-20:00 (mean±standard deviation, n=12).

Example 7: Effects of the Compound of Example 2 on Rats with Diabetes Accompanied by Hypertension After 4 weeks of administering the compound of Example 2, the rats of model group showed an average systolic pressures during time period 10:00-20:00 significantly higher than that of the normal control group (NC group). The compound of Example 2 showed an average systolic pressures during time period 10:00-20:00 significantly lower than that of the model group (169.8:15.8 mmHg vs. 181±14.9 mmHg, P<0.05) (see details in FIG. 6).

Figure 7:
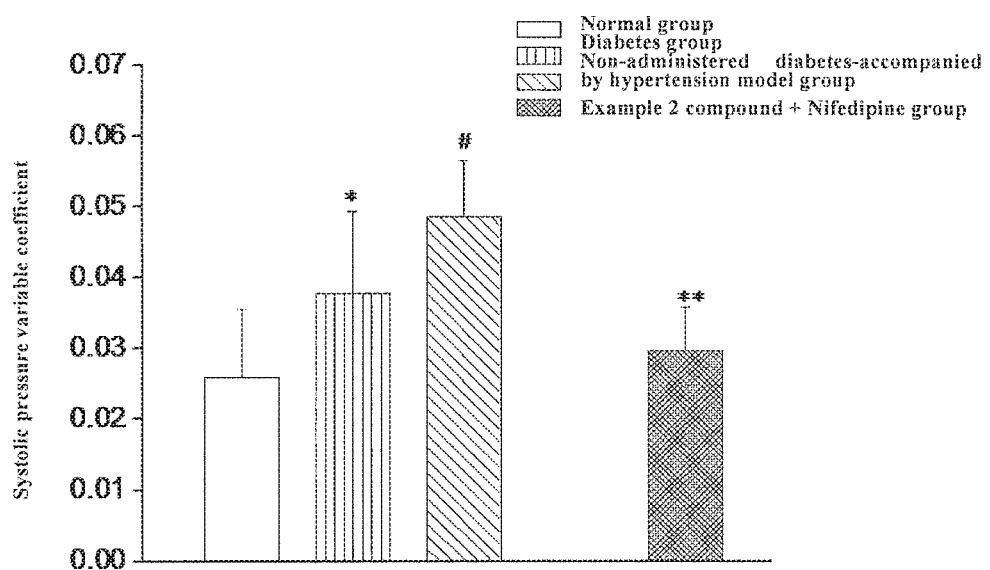
FIG. 7: systolic pressure variable coefficients of different groups during time period 10:00-20:00 (mean±standard deviation, n=12.*$P<0.05$, #$P<0.01$ vs. normal group; **$P<0.01$ vs. model).

After 4 weeks of administering the compound of Example 2, the rats of diabetes group showed a systolic pressure variable coefficient (CV) during time period 10:00-20:00 significantly higher than that of the NC group (P<0.05), while the rats of the model group showed a further significantly increase in systolic pressure CV (P<0.01). In comparison with the model group, the rats of the group of the compound of Example 2 showed a significantly decrease in systolic pressure CV (P<0.01) (see details in FIG. 7).

Figure 8:
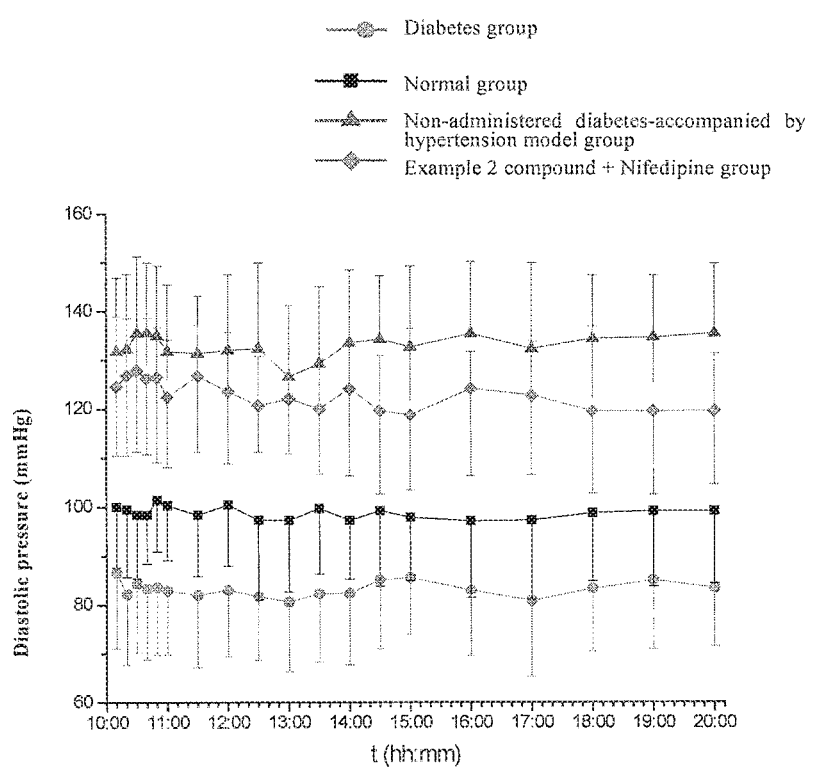
FIG. 8: diastolic pressure dynamic curves of different groups during time period 10:00-20:00.

After 4 weeks of administering the compound of Example 2, the rats of model group showed a significant increase in average systolic pressure during time period 10:00-20:00 in comparison with the NC group. In comparison with the model group, the group of the compound of Example 2 showed a significantly decrease in average systolic pressure during time period 10:00-20:00 (123.1±13.4 mmHg vs. 132.3±12.7 mmHg) (see details in FIG. 8).

Figure 9:
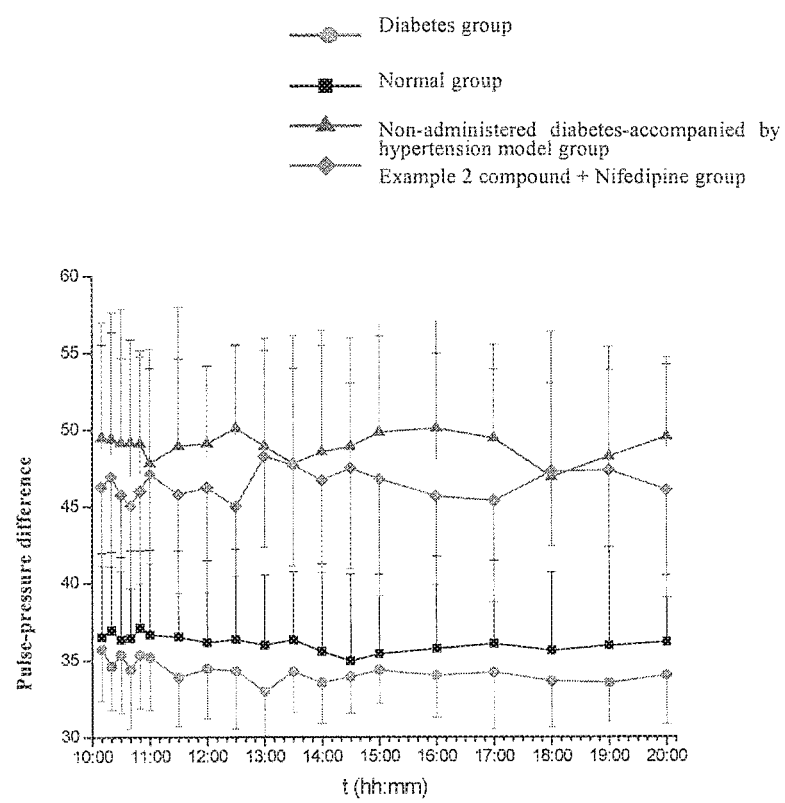
FIG. 9: pulse pressure dynamic curves of different groups during time period 10:00-20:00.

After 4 weeks of administering the compound of Example 2, the rats of model group showed a significant increase in average pulse-pressure difference during time period 10:00-20:00 in comparison with the NC group (P<0.01). In comparison with the model group, the group of the compound of Example 2 showed no significant change (46.5±5.7 mmHg vs. 49.7±3.5 mmHg) (see details in FIG. 9).

Figure 10:
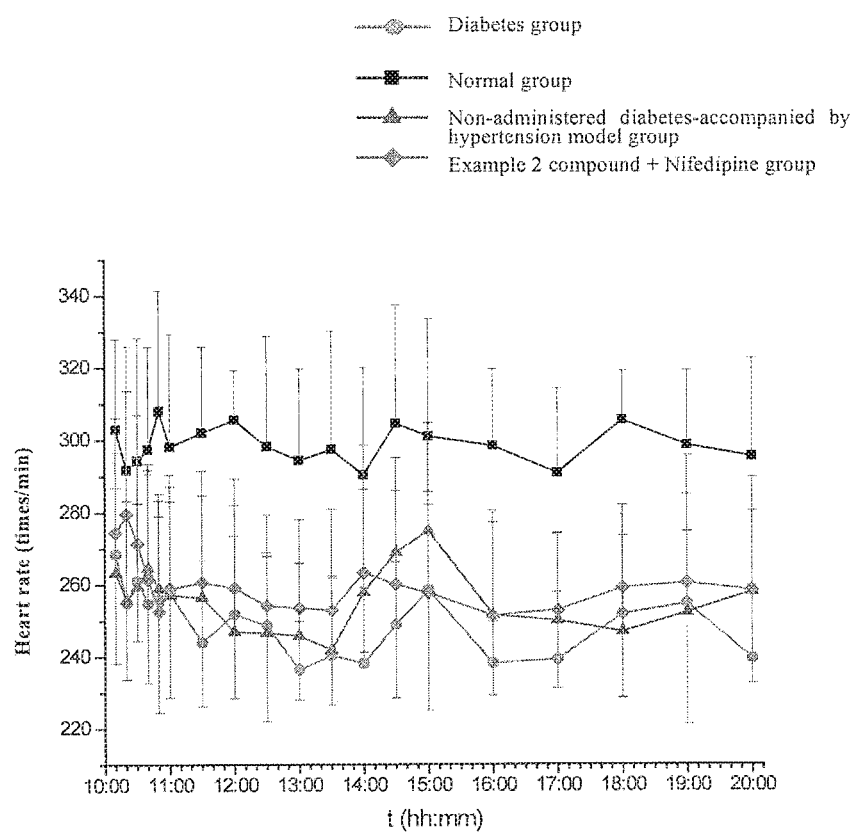
FIG. 10: heart rate dynamic curves of different groups during time period 10:00-20:00.

After 4 weeks of administering the compound of Example 2, the rats of model group showed a significant decrease in average heart rate during time period 10:00-20:00 in comparison with the NC group (P<0.01). In comparison with the model group, the group of the compound of Example 2 showed no significant change (255±17 vs. 257±13 beats/min) (see details in FIG. 10).

The results of Example 7 show that the compound of Example 2 has effects of stabilizing blood pressure, conforming to the therapeutic principle of diabetes accompanied by hypertension, and may act as an adjuvant drug for enhancing blood pressure stability in anti-hypertension drug combination.

Figure 11:
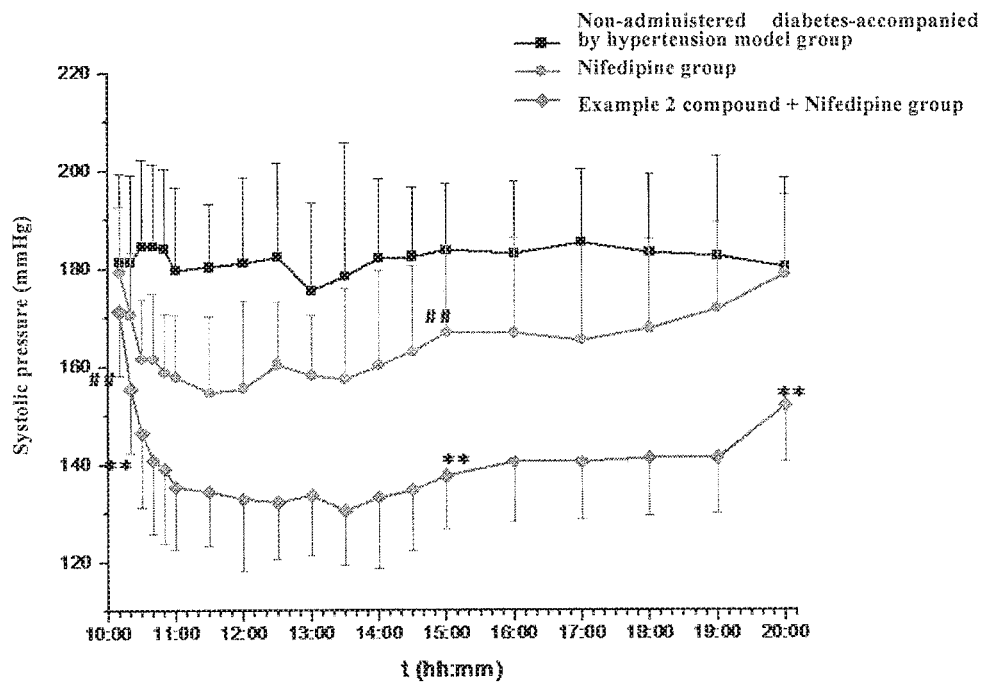
FIG. 11: systolic pressure dynamic curves of different groups during time period 10:00-20:00 (M mean±standard deviation, n=12. ##$P<0.01$ vs. model group; **$P<0.01$ vs. Nifedipine group).

Example 8: Effects of the Compound of Example 2 in Combination with Nifedipine on Rats with Diabetes Accompanied by Hypertension After administration of Nifedipine at 10:00, the systolic pressures of the administration groups dropped quickly, and reached the maximum of pressure drop after 1.5 h; the Nifedipine group showed the systolic pressure stated to rise after 2 h of administration, and the systolic pressure was substantially close to that of the model group after 10 h; the Example 2 compound+Nifedipine group showed the systolic pressure could keep stable for 5 h after reaching the lowest value, and then slowly recovered. In comparison with the Nifedipine group, the Example 2 compound+Nifedipine group showed a significant decrease in average systolic pressure after administration for 1 h (135.8±12.5 mmHg vs. 155.2±14.9, P<0.01); 5 h (135.0±11.4 mmHg vs. 166.0±15.0 mmHg, P<0.01), 10 h (152.2±10.4 mmHg vs. 179.0±14.1 mmHg, P<0.01) (see details in FIG. 11).

Figure 12:
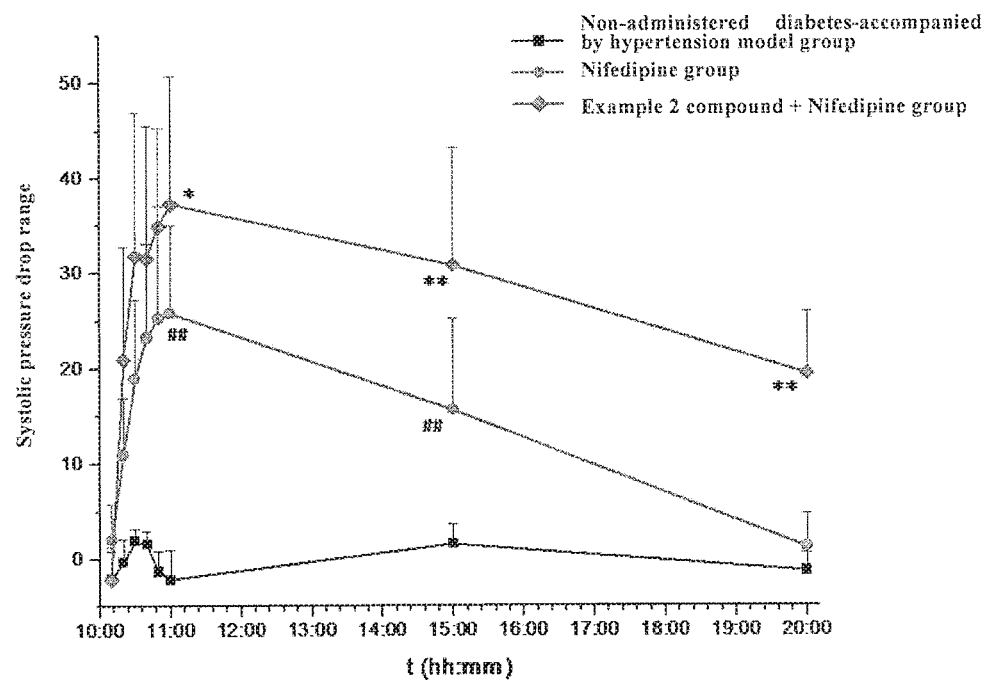
FIG. 12: systolic pressure drop scope dynamic curves of different groups during time period 10:00-20:00 (mean±standard deviation, n=12. ##$P<0.01$ vs. model group; *$P<0.05$, **$P<0.01$ vs. Nifedipine group).

After administration for 1.5 h, the Example 2 compound+Nifedipine group showed a pressure drop ΔSBP significantly higher than that of the Nifedipine group (37.1±13.5 mmHg vs. 25.3±9.3 mmHg, P<0.05). After administration for 5 h, the Example 2 compound+Nifedipine group showed a ΔSBP significantly higher than that of the Nifedipine group (30.9-12.5 mmHg vs. 15.9±9.3 mmHg, P<0.01), and after administration for 10 h, the Example 2 compound+Nifedipine group showed a ΔSBP significantly higher than that of the Nifedipine group (19.4±16.4 mmHg vs. 1.19±3.5 mmHg, P<0.01) (see details in FIG. 12).

Figure 13:
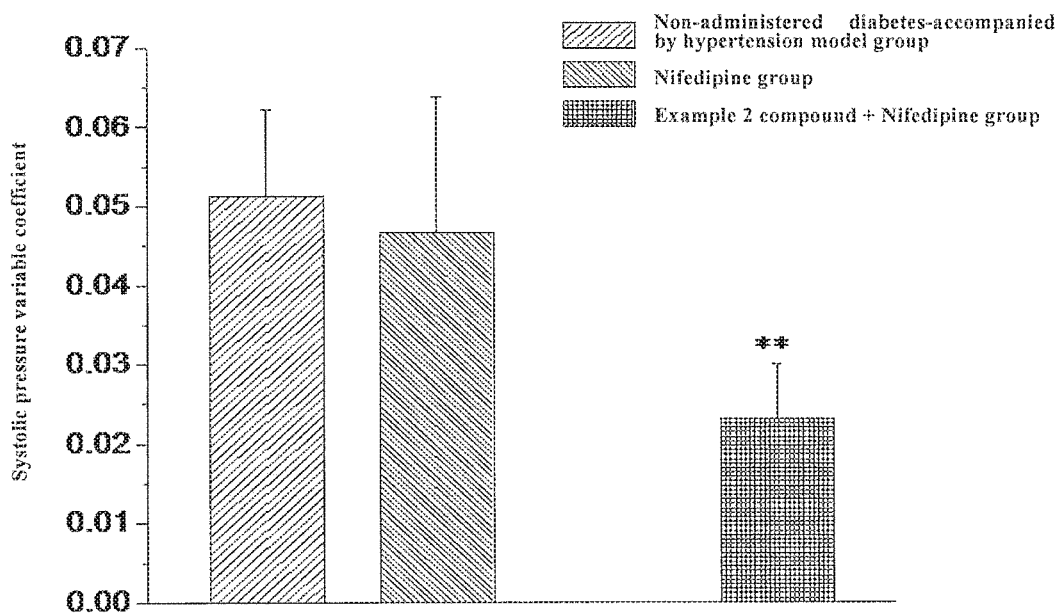
FIG. 13: systolic pressure variable coefficient dynamic curves of different groups during time period 11:00-15:00 (mean±standard deviation, n=12. **$P<0.01$ vs. model group).

After administration for 1-5 h, in comparison with the model group, the Nifedipine group showed no significant systolic pressure variable coefficient (CV) (0.047±0.017 vs. 0.051±0.012), the Example 2 compound+Nifedipine group showed a significant decrease in CV (0.019±0.006 vs. 0.051±0.012, P<0.01) (see details in FIG. 13).

Figure 14:
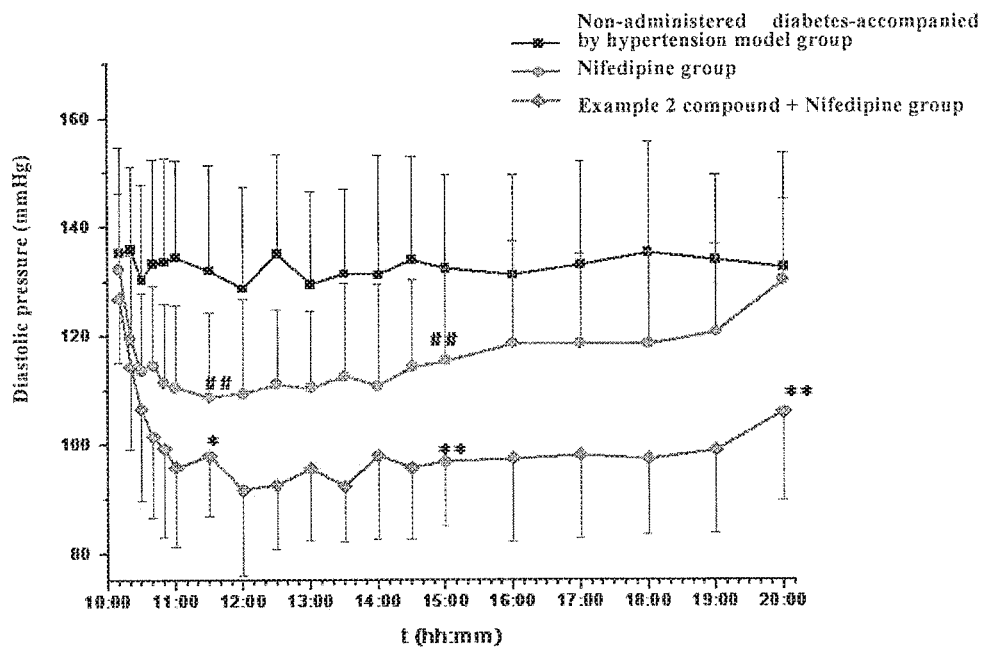
FIG. 14: diastolic pressure dynamic curves of different groups during time period 10:00-20:00 (mean±standard deviation, n=12. ##$P<0.01$ vs. model group; *$P<0.05$, **$P<0.01$ vs. Nifedipine group).

After administration at 10:00, the systolic pressures of the administration groups showed a quick decrease, and almost reached the maximum pressure drop range after 1.5 h, then slowly recovered. After administration for 1.5 h, the Example 2 compound+Nifedipine group showed a significant decrease in average systolic pressure in comparison with the Nifedipine group (95.8±14.5 mmHg vs. 111.2±15.3, P<0.05). After administration for 5 h, the Example 2 compound+Nifedipine group showed a significant decrease in average systolic pressure in comparison with the Nifedipine group (96.6±12.3 mmHg vs. 115.9±15.7 mmHg, P<0.01). After administration for 10 h, the Nifedipine group showed a diastolic pressure close to that of the model group, the Example 2 compound+Nifedipine group showed a significant decrease in average systolic pressure in comparison with the Nifedipine group (106.1±16.4 mmHg vs. 130.1±14.8 mmHg, P<0.01) (see details in FIG. 14).

Figure 15:
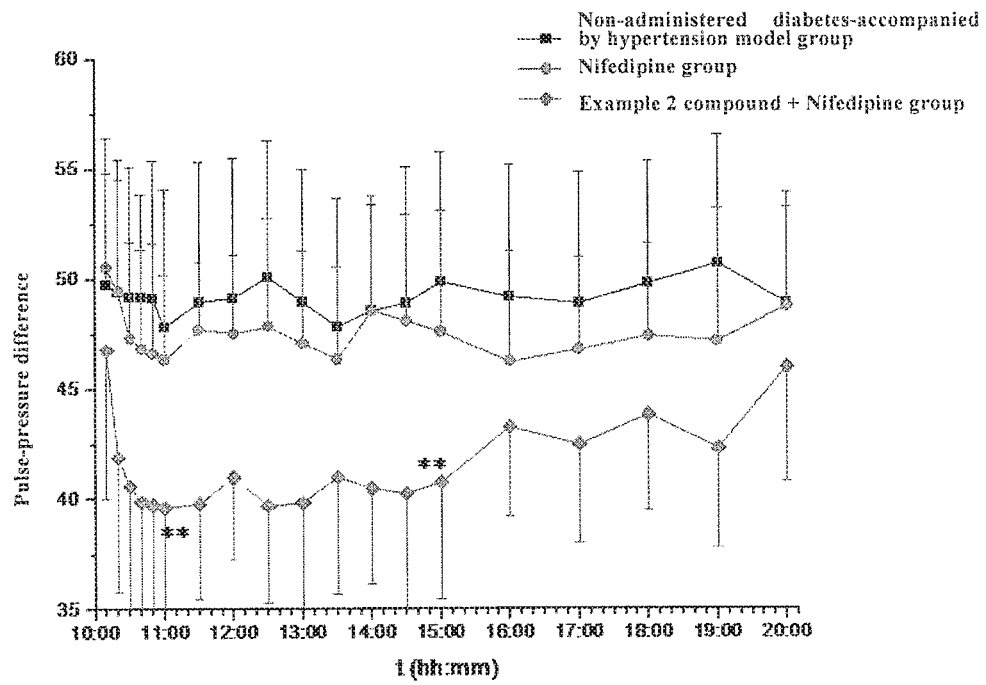
FIG. 15: pulse pressure dynamic curves of different groups during time period 10:00-20:00 (mean±standard deviation, n=12. **$P<0.01$ vs. Nifedipine group).

After administration at 10:00, the Example 2 compound+Nifedipine group showed a rapid decrease in pulse-pressure difference (PH), which reached the maximum of pressure drop at 11:00; the Nifedipine group showed a slight decrease of PH, which started to rise after 1 h, and almost reached that of the model group after 10 h; the Example 2 compound+Nifedipine e group reached the lowest value of PH after 1 h, which started to rise slowly since then. After administration for 1 h, the Example 2 compound+Nifedipine group showed a significant decrease in average pulse-pressure difference in comparison with the Nifedipine group (40.2±4.5 vs. 46.9-2.9 mmHg, P<0.01). After administration for 5 h, the Example 2 compound+Nifedipine group showed a significant decrease in average pulse-pressure difference in comparison with the Nifedipine group (40.6±4.9 vs. 48.1±5.1 mmHg, P<0.01). After administration for 10 h, the Example 2 compound+Nifedipine group showed no change in average pulse-pressure difference in comparison with the Nifedipine group (45.6±5.8 vs. 48.7±5.2 mmHg) (see details in FIG. 15).

Figure 16:
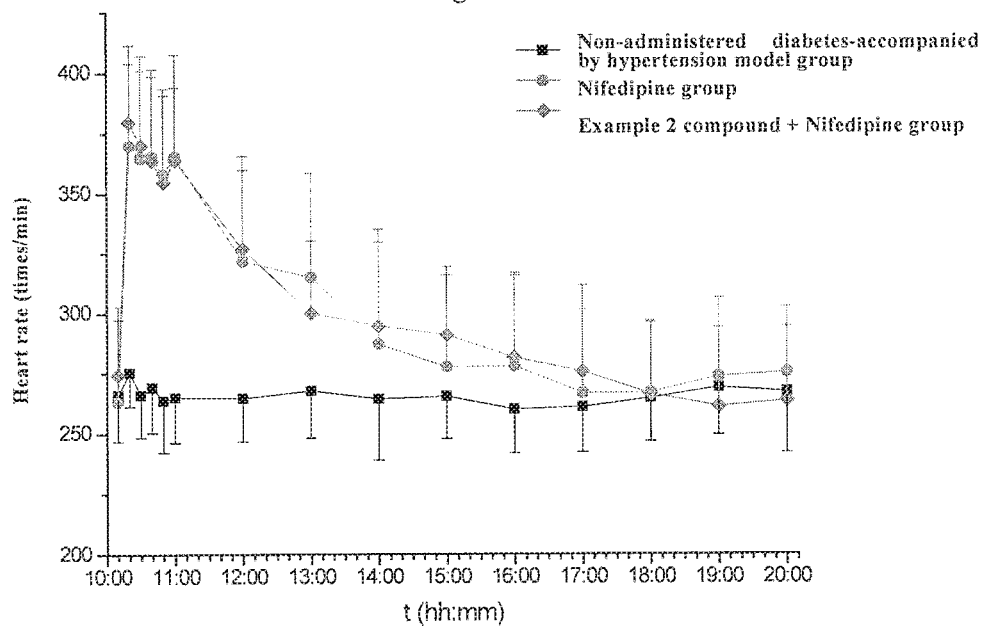
FIG. 16: heart rate dynamic curves of different groups during time period 10:00-20:00.

After administration at 10:00, the administration groups showed a rapid increase in heart rate (HR), which reached the maximum after 20 min, then started to drop slowly, after administration for 8 h, the heart rate of the administration groups substantively recovered the level before administration. After administration, the Example 2 compound+Nifedipine group showed no change in heart rate in comparison with the Nifedipine group (see details in FIG. 16).

Figure 17:
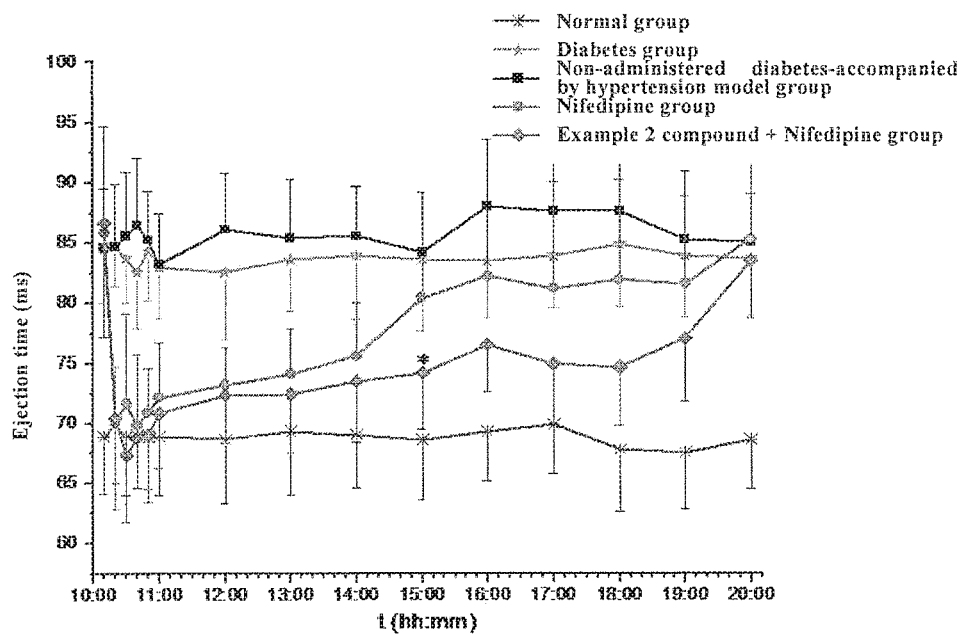
FIG. 17: ejection time dynamic curves of different groups during time period 10:00-20:00 (mean±standard deviation, n=12. *$P<0.05$ vs. Nifedipine group).

After administration at 10:00, the administration groups showed a rapid decrease in ejection time (ET), which reached the lowest value after 20 min, then started to rise slowly; after administration for 5 h, the ET of the Nifedipine group substantively recovered the level before administration; after administration for 10 h, the Nifedipine group showed a ET value substantively equivalent to that of the MC group. After administration for 20 min, the Example 2 compound+Nifedipine group showed a significant decrease in ET in comparison with the Nifedipine group (67.3±5.3 ms vs. 71.8±4.2 ms), then the ET started to rise slowly, and showed a rapid increase stage after 8-10 h, and reached to a ET level substantively equivalent to that of the MC group after 10 h; after administration for 5 h, the Example 2 compound+Nifedipine group showed a significant decrease in ET in comparison with the Nifedipine group (74.2±5.2 ms vs. 81.1±5.0 ms, P<0.05), and this effect kept for 4 h (see details in FIG. 17).

Figure 18:
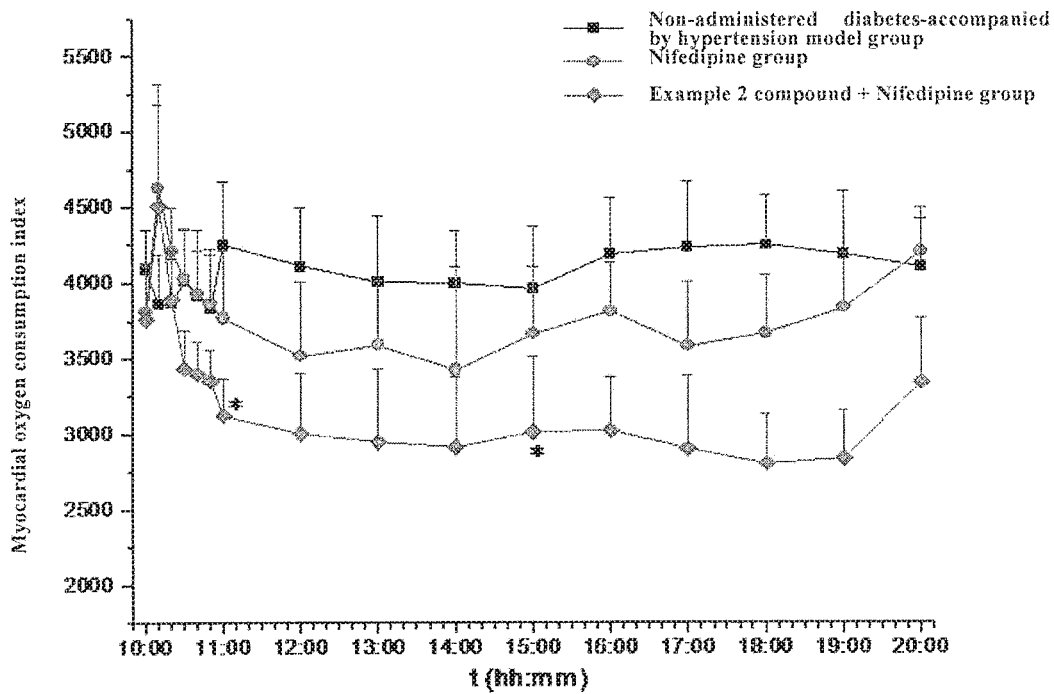
FIG. 18: muscular oxygen uptake index dynamic curves of different groups during time period 10:00-20:00 (mean±standard deviation, n=12. *$P<0.05$ vs. Nifedipine group).

Myocardial oxygen consumption index (MOCI) reflects total myocardial oxygen consumption. After administration for 1 h, in comparison with the model group, the Nifedipine group showed a decrease in MOCI, without significant difference (3772.7±444.7 vs. 4255.0±416.1, P=0.36), while the Example 2 compound+Nifedipine group showed a significant decrease in MOCI (3128.4±238.7 vs. 4255.0±416.1, P<0.05). After administration for 5 h, in comparison with the model group, the Nifedipine group showed a decrease in MOCI, without significant difference, the Example 2 compound+Nifedipine group showed a significant decrease in MOCI (P<0.05). After administration for 10 h, the Nifedipine group showed a MOCI recovered to the level before administration, the Example 2 compound+Nifedipine group showed a MOCI lower than that of the model group and the Nifedipine group, without significant difference (see details in FIG. 18).

The results of Example 8 showed that the compound of Example 2 can significantly enhance the effects of Nifedipine on heart; and the compound of Example 2 in combination with Nifedipine could significantly reduce the blood pressure of rats with diabetes accompanied by hypertension.

Figure 19:
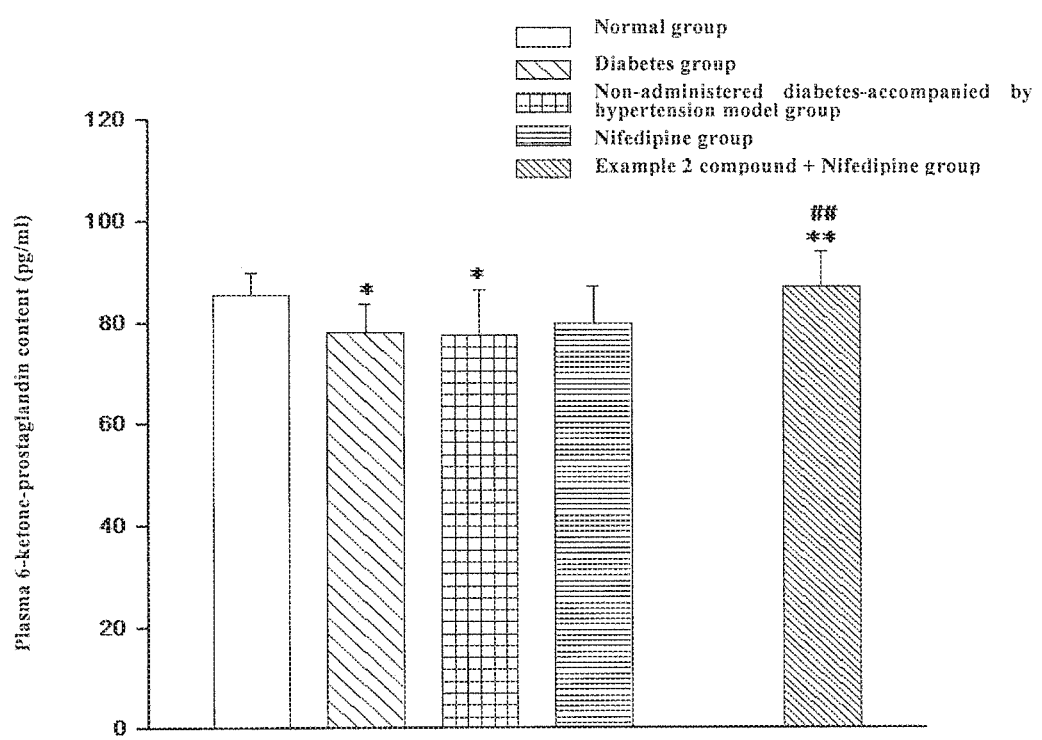
FIG. 19: plasma 6-ketone-prostaglandin content of different groups (mean±standard deviation, n=9-11. *$P<0.05$ vs. normal group; **$P<0.01$ vs. model group; ##$P<0.05$ vs. Nifedipine group).

Example 9: Effects of the Compound of Example 2 in Combination with Nifedipine on Vascular Active Factors Content in Rats with Diabetes Accompanied by Hypertension (1) Effects of the Compound of Example 2 in Combination with Nifedipine on Plasma 6-Ketone Prostaglandin Content in Rats with Diabetes Accompanied by Hypertension Plasma 6-ketone-prostaglandin is a metabolite of prostacyclin ($PGI_2$), reflecting the $PGI_2$ content in plasma. In comparison with the diabetes group, the rats of the model group showed a significant decrease in plasma 6-ketone-prostaglandin content in comparison with the normal group (78.15±5.6, 77.62±8.67 vs. 85.41±4.36 pg/mL, P<0.05). The rats of the Example 2 compound+Nifedipine group showed a significant increase in comparison with the model group (87.21±6.90 vs. 77.62±8.67 pg/mL, P<0.01), and a significant increase in comparison with the Nifedipine group as well (P<0.05) (see details in FIG. 19).

Figure 20:
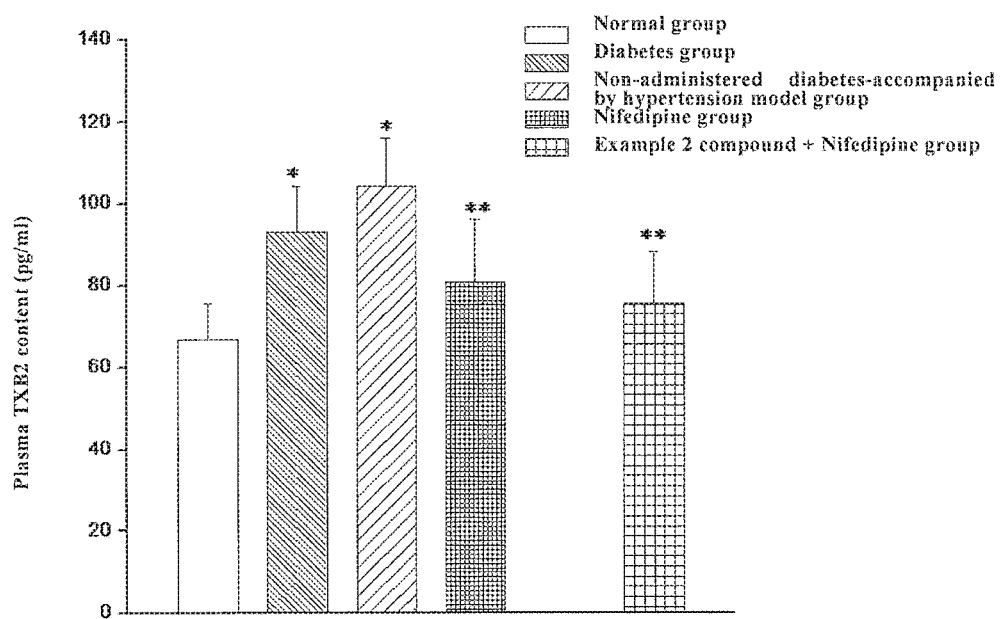
FIG. 20: plasma $TXB_2$ content of different groups (mean±standard deviation, n=9-11. *$P<0.01$ vs. normal group; **$P<0.01$ vs. model group).

(2) Effects of AGEs Breaker in Combination with Nifedipine on $TXB_2$ Content in Plasma of Rats with Diabetes Accompanied by Hypertension $TXB_2$ is a metabolite of $TXA_2$, and reflects $TXA_2$ contents in plasma. In comparison with the normal group, the rats of the diabetes group and the model group showed a significant increase in $TXB_2$ content (93.14±10.99, 104.19±11.68 vs. 64.88±7.24, P<0.01). The Example 2 compound+Nifedipine group and the Nifedipine group showed a significant decrease in $TXB_2$ content in comparison with the model group (73.64±12.27, 80.88±15.31 vs. 104.19±11.68 pg/mL, P<0.01); The Example 2 compound+Nifedipine group showed no significant difference in $TXB_2$ content in comparison with the Nifedipine group (see details in FIG. 20).

Figure 21:
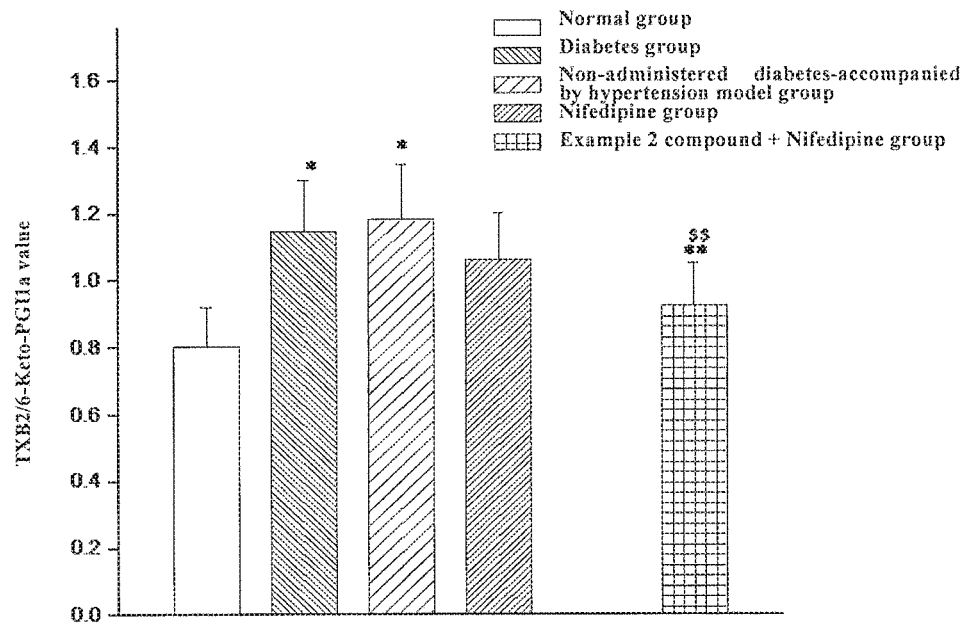
FIG. 21: $TXB_2$/6-Keto-PGI1a values of different therapeutic groups (mean±standard deviation, n=9-11. *$P<0.01$ vs. normal group; **$P<0.01$ vs. model group; $^{\$\$}P<0.05$ vs. Nifedipine group).

(3) Effects of the Compound of Example 2 in Combination with Nifedipine on Plasma $TXB_2$/6-Keto-PGI1a Ratio of Rats with Diabetes Accompanied by Hypertension $TXB_2$/6-Keto-PGI1a ratio reflects the level of plasma $TXA_2/PGI_2$. In comparison with the normal group, the rats of the diabetes group and the model group showed significant increase in $TXB_2$/6-Keto-PGI1a (1.15±0.15, 1.18±0.16 vs. 0.80±0.10, P<0.01); the Example 2 compound+Nifedipine group showed a significant decrease in TXB2/6-Keto-PGI1a in comparison with the model group (0.93±0.13 vs. 1.18-0.16, P<0.01); the Nifedipine group showed a slightly decrease in comparison with the model group (1.06±0.14 vs. 1.18±0.16), without significant difference; the Example 2 compound+Nifedipine group showed a significant decrease in $TXB_2$/6-Keto-PGI1a in comparison with the Nifedipine group (0.93±0.13 vs. 1.06±0.14, P<0.05) (see details in FIG. 21).

Figure 22:
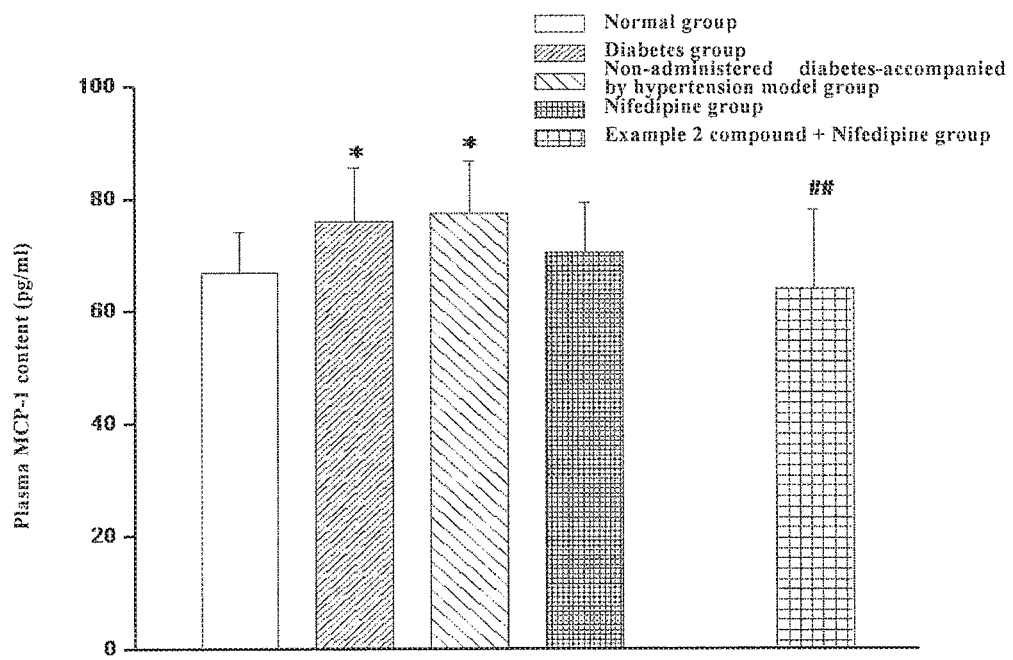
FIG. 22: plasma MCP-1 contents of different therapeutic groups (mean±standard deviation, n=9-11. *$P<0.05$ vs. normal group; ##$p<0.01$ vs. model group).

(4) Effects of the Compound of Example 2 in Combination with Nifedipine on Plasma MCP-1 Content in Rats with Diabetes Accompanied by Hypertension In comparison with the normal group, the rats of the diabetes groups and the model group showed a significant increase in plasma MCP-1 content (75.9±9.7, 77.4±9.5 vs. 66.9±7.3 pg/mL, P<0.05); the Example 2 compound+Nifedipine group showed a significant decrease in plasma MCP-1 content in comparison with the model group (64.0±14.2 vs. 77.4-9.5 pg/mL, P<0.01); the Nifedipine group showed a slight decrease in plasma MCP-1 content in comparison with the model group (70.7-8.8 vs. 77.4-9.5 pg/mL), without significant difference; the Example 2 compound+Nifedipine group showed a significant decrease in plasma MCP-1 content in comparison with the Nifedipine group (P<0.05) (see details in FIG. 22).

Figure 23:
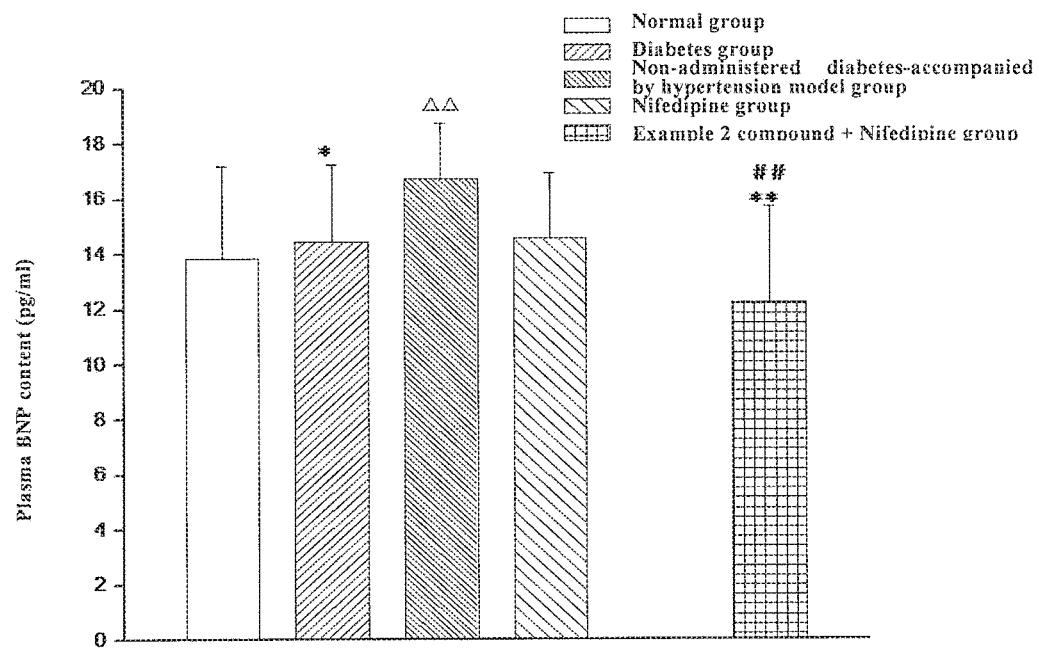
FIG. 23: plasma BNP content of different therapeutic groups (mean±standard deviation, n=9-11. *$P<0.05$ vs. normal group; $^{\triangle\triangle}p<0.05$, **$p<0.01$ vs. model group; ##$p<0.01$ vs. Nifedipine group).

(5) Effects of the Compound of Example 2 in Combination with Nifedipine on Plasma BNP Content in Rats with Diabetes Accompanied by Hypertension In comparison with the normal group, the rats of the model group showed a significant increase in plasma BNP content (16.7±2.0 vs. 14.3±2.1 pg/mL, P<0.05); the Example 2 compound+Nifedipine group showed a significant decrease in plasma BNP content in comparison with the model group (12.2±3.5 vs. 16.7±2.0 pg/ml, P<0.01); the Nifedipine group showed a significant decrease in plasma BNP content in comparison with the model group (14.6±2.4 vs. 16.7-2.0 pg/mL, P<0.05); the Example 2 compound+Nifedipine group showed a significant decrease in plasma MCP-1 content in comparison with the Nifedipine group (P<0.05, P<0.01)(see details in FIG. 23).

The results of Example 9 showed that the compound of Example 2 resulted in decrease in TXA$_2$/PGI$_2$ ratio, vascular dilatation, reduction of thrombosis, delaying atherosclerosis procedure, and vascular protection. The AGEs breaker can also reduce plasma BNP content in rats with diabetes accompanied by hypertension, and significantly reduce plasma MCP-1 content in rats with diabetes accompanied by hypertension.

Although the specific models of the present invention have been described in details in the specific models of the present invention, the skilled in the art would understand those details could be modified and replaced according the disclosures, and all of these changes fall within the protection scope of the present invention. The protection scope of the present invention is given by the appended claims and any equivalents thereof.

What is claimed is:

1. A method for preparing the compound of Formula I, comprising the following steps:

Compound A is reacted with 1,2-epoxypropane to obtain Compound B,

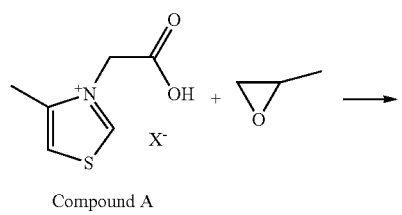

Compound A

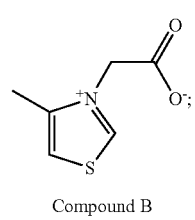

Compound B wherein, in the structure of Compound A, X is chlorine, bromine or iodine;

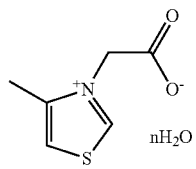

Formula I wherein:
n is 0, 1, 2 or 3;
wherein when n is 0 the compound of Formula I is Compound B; and
wherein when n is 1, 2, or 3 the compound of Formula I is prepared from Compound B through the following steps: Compound B is dissolved in methanol followed by dropwise addition of ethyl acetate and the mixture is left to stand to obtain monocrystals of the compound of Formula I.

2. The method according to claim 1, wherein Compound A is prepared via the following steps:
4-methylthiazole is reacted with chloroacetic acid, bromoacetic acid or iodoacetic acid to obtain Compound A,

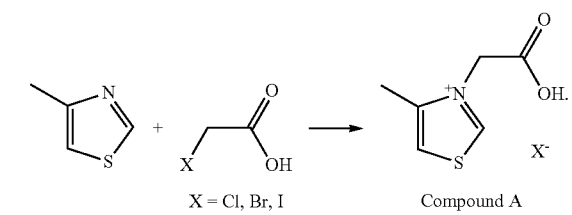

3. The method according to claim 2, wherein Compound A is separated and purified via recrystallization.

4. A method for preparing monocrystals of the compound of Formula I, comprising the following steps:
3-methylcarbonyloxy-4-methyl-thiazole inner salt is dissolved in methanol followed by dropwise addition of ethyl acetate and the mixture is left to stand to obtain monocrystals;

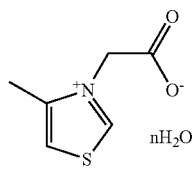

Formula I wherein:
n is 0, 1, 2 or 3.

5. The method according to claim 3, wherein the solvent used for recrystallization is any one independently selected from the group consisting of acetone, methanol, ethanol, ethyl ether, petroleum ether, and n-hexane, or any mixture thereof.

6. The method according to claim 4, wherein for 1 mg of 3-methylcarbonyloxy-4-methyl-thiazole inner salt, 0.05 mL methanol and 0.3 mL ethyl acetate are used.

7. The method according to claim 1, wherein Compound B is separated and purified via recrystallization.

8. The method according to claim 7, wherein the solvent used for recrystallization is any one independently selected from the group consisting of acetone, methanol, ethanol, ethyl ether, petroleum ether, and n-hexane, or any mixture thereof.

* * * * *